United States Patent [19]

Maravetz

[11] Patent Number: 5,198,014
[45] Date of Patent: Mar. 30, 1993

[54] HERBICIDAL BETA-PYRAZOLYLACRYLIC ACID COMPOUND

[75] Inventor: Lester L. Maravetz, Westfield, N.J.

[73] Assignee: FMC Corporation, Philadelphia, Pa.

[21] Appl. No.: 795,403

[22] Filed: Nov. 20, 1991

[51] Int. Cl.⁵ .................... A01N 43/56; C07D 231/38
[52] U.S. Cl. ..................................... 504/225; 544/124; 546/279; 504/253; 504/271; 504/280; 504/177; 504/181; 504/178
[58] Field of Search ........................ 544/124; 546/279; 71/92

[56] References Cited

U.S. PATENT DOCUMENTS

| | | | |
|---|---|---|---|
| 4,435,208 | 3/1984 | Forster et al. | 71/105 |
| 4,459,150 | 7/1984 | Hatton et al. | 71/92 |
| 4,496,390 | 1/1985 | Hatton et al. | 71/92 |
| 4,563,210 | 1/1986 | Beck et al. | 71/92 |
| 4,629,495 | 12/1986 | Hatton et al. | 71/92 |
| 4,685,956 | 8/1987 | Gehring et al. | 71/92 |
| 4,685,957 | 8/1987 | Gehring et al. | 71/92 |
| 4,770,688 | 9/1988 | Gehring et al. | 71/86 |
| 4,770,692 | 9/1988 | Stetter et al. | 71/92 |
| 4,770,693 | 9/1988 | Gehring et al. | 71/92 |
| 4,772,312 | 9/1988 | Schallner et al. | 71/92 |
| 4,787,930 | 11/1988 | Gehring et al. | 71/92 |

FOREIGN PATENT DOCUMENTS 2136427 5/1984 United Kingdom ................. 71/92

*Primary Examiner*—C. Warren Ivy
*Assistant Examiner*—Zinna N. Davis
*Attorney, Agent, or Firm*—H. R. Ertelt; R. M. Kennedy

[57] ABSTRACT

This application discloses hebricidal B-pyrazolylacrylic acids, compositions containing them, methods of preparing them, and methods for controlling undesired plant growth by preemergent or postemergent application of the herbicidal compositions to the locus where control is desired. The herbicidal compounds have the formula

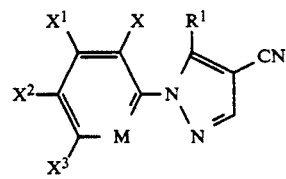

in which the radicals are defined in the claims.

12 Claims, No Drawings

HERBICIDAL BETA-PYRAZOLYLACRYLIC ACID COMPOUND

This invention pertains to novel B-pyrazolyacrylic acids and their use for weed control in agriculture, horticulture, and other fields in which it is desired to control unwanted plant growth, such as grassy or broadleaf plant species In particular it pertains to 3-[4-cyano-1-(substituted-phenyl or -pyridyl)-1H-pyrazol-5-yl]acrylates as pre- and postemergence herbicides. The use of this class of herbicides is heretofore unknown.

A variety of herbicidal 1-arylpyrazoles have previously been described. For example, U.S. Pat. No. 4,459,150 describes the use as herbicides of compounds of the following structure:

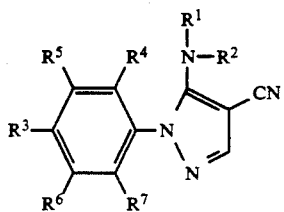

wherein $R^1$ represents $R^8C(=O)$—wherein $R^8$ represents H, $C_{1-7}$ alkyl or $C_{1-4}$ alkoxy optionally substituted by $C_{1-4}$ alkoxy, $C_{2-5}$ alkoxycarbonyl or halogen, $C_{3-4}$ alkenyloxy, $C_{3-6}$ cycloalkyl optionally substituted by $CH_3$ or $C_2H_5$, or phenoxy, $R^2$ represents H or $R^8C(=O)$—, or $R^1$ and $R^2$ together represent —CO—$(CR^1R^b)_m$—CO—, $R^3$ represents F, Cl, Br, $C_{1-4}$ alkyl optionally substituted by halogen, or $C_{2-4}$ alkenyl, $R^4$ represents F, Cl, Br, $NO_2$, $CH_3$ or $C_2H_5$ and $R^5$, $R^6$ and $R^7$ represent H, F, Cl, Br, $NO_2$, $CH_3$ or $C_2H_5$, or $R^4$ and $R^5$ each represent Cl and $R^3$, $R^6$ and $R^7$ each represent H, $R^a$ and $R^b$ represent H or $C_{1-4}$ alkyl, and m is 2 or 3. British Patent Application 2136427A describes the following herbicidal N-pyridylpyrazole derivatives:

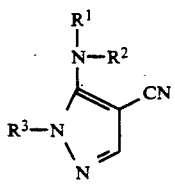

wherein $R^1$ is hydrogen, $R^4C(=O)$—, or $R^5$ ($R^5$ is amongst others $C_{1-8}$ alkyl); $R^2$ is hydrogen when $R^1$ is hydrogen, or $R^4C(=O)$- when $R^1$ is $R^4C(=O)$—, or hydrogen or $R^5$ when $R^1$ is $R^5$, or $R^1$ and $R^2$ may be taken together to form ring systems, and $R^3$ is 3-chloro-5-trifluoromethylpyridin-2-yl.

U.S. Pat. No. 4,496,390 describes the following N-phenylpyrazole derivatives as herbicides:

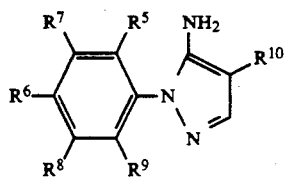

wherein each of $R^5$ and $R^6$ represents a $C_{1-4}$ alkyl or alkoxy radical, a trifluoromethyl, trifluoromethoxy, nitro, cyano or primary amino radical, or a fluorine, chlorine or bromine atom, each of $R^7$, $R^8$ and $R^9$ represents a hydrogen atom, a $C_{1-4}$ ifluoromethoxy, nitro, cyano or primary amino radical or a fluorine, chlorine or bromine atom, or $R^5$, $R^7$, $R^8$ and $R^9$ each represents a hydrogen atom and $R^6$ represents a trifluoromethoxy or trifluoromethyl radical, and $R^{10}$ represents a cyano radical or substituted carbamoyl radical —CONHR$^{11}$, wherein $R^{11}$ represents a methyl or ethyl radical.

U.S. Pat. No. 4,563,210 discloses the following herbicidal 5-halo-1-halophenyl-1H-pyrazole-4-carbonitriles:

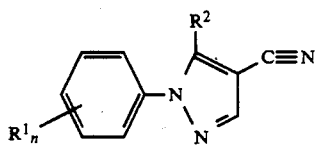

wherein each $R^1$ independently is halogen; $R^2$ is halo or trifluoromethyl; and n is 1-5; with the provisos that when n is 1, $R^1$ is other than fluorine, and when n is 2 and each $R^1$ is chlorine, at least one $R^1$ is located at a para or ortho position on the phenyl ring.

U.S. Pat. No. 4,629,495 disclose 5-amino-4-cyano-1-phenylpyrazoles:

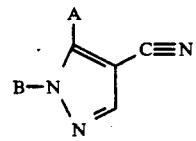

wherein A represents $R^1R^2N$- wherein $R^1$ represents $C_{1-8}$ alkyl or $C_{2-8}$ alkenyl or alkynyl unsubstituted or substituted by CN, OH, $C_{1-6}$ alkoxy, carboxy, $C_{2-9}$ alkoxycarbonyl, aminocarbonyl optionally substituted by $C_{1-8}$ alkyl or $C_{2-8}$ alkenyl, $C_{1-8}$ alkoxyaminocarbonyl, $C_{1-8}$ alkanesulphonamidocarbonyl, —C(=O)-Het, where Het represents a nitrogen-containing heterocyclic group, or one or more halogen atoms or $R^1$ represents $C_{3-6}$ cycloalkyl optionally substituted by $C_{1-4}$ alkyl and $R^2$ represents H or $R^1$, or $R^1$ represents $C_{1-4}$ alkylthio and $R^2$ represents H, or A represents $R^p(R^q)$—C=N— (wherein $R^q$ represents $C_{1-4}$ alkoxy or amino substituted by one or two $C_{1-4}$ alkyl groups and $R^q$ represents H or $C_{1-4}$ alkyl) or A represents 2-oxoazetidin-1-yl, 2-oxo-pyrrolidin-1-yl or 2-oxopiperidin-1-yl optionally substituted by $C_{1-6}$ alkyl or A represents open-chain alkenylcarbonylamino and B represents phenyl substituted in the 2-position by F, Cl, Br, $NO_2$, —$CH_3$ or —$C_2H_5$ and in the 4-position by F, Cl, Br, $C_{1-4}$ (optionally substituted by halogen) or $C_{2-4}$ alkenyl and alkynyl and optionally substituted in the 3-, 5- and 6-positions by F, Cl, Br, $NO_2$, —$CH_3$ or —$C_2H_5$, or B represents 2,3-dichlorophenyl, and salts thereof.

U.S. Pat. No. 4,685,956 discloses the following 1-aryl-5-hydrazinopyrazoles, compositions containing them, and herbicidal methods of using them:

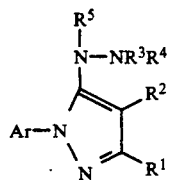

in which $R^1$ represents hydrogen or alkyl;

$R^2$ represents cyano or nitro;

$R^3$ represents hydrogen, or represents in each case optionally substituted alkyl, alkenyl, alkynyl or cycloalkyl, or represents a radical —C(=X)—$R^6$, or represents a radical —SO$_2$—$R^7$;

$R^4$ represents hydrogen, or represents in each case optionally substituted alkyl, alkenyl, alkynyl or cycloalkyl, or represents a radical —C(=X)—$R^6$, or represents a radical —SO$_2$—$R^7$;

$R^5$ represents hydrogen or, in the case where $R^4$ represents hydrogen, also represents a radical —C(=X)—$R^6$, or represents a radical —SO$_2$—$R^7$, or represents in each case optionally substituted alkyl, alkenyl, alkynyl or cycloalkyl, wherein, in each case;

X represents oxygen or sulfur, $R^6$ represents hydrogen, alkyl, alkoxy, alkoxyalkyl, alkylthio, alkylthioalkyl, alkylamino, dialkylamino, halogenoalkyl, alkenyl or alkynyl, or represents optionally substituted cycloalkyl, or represents in each case optionally substituted aryl, aryloxy, arylthio or arylamino and;

$R^7$ represents alkyl, hydroxyalkyl, alkoxyalkyl, halogenoalkyl, alkenyl, alkynyl or cycloalkyl, or represents in each case optionally substituted aralkyl or aryl and;

Ar represents substituted phenyl, or represents optionally substituted pyridyl.

U.S. Pat. No. 4,685,957 disclose the following 1-aryl-5iminoaminopyrazoles, compositions containing them, and herbicidal methods of using them:

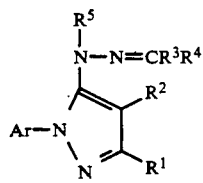

in which $R^1$ represents hydrogen or alkyl, $R^2$ represents cyano or nitro, $R^3$ and $R^4$ independently of one another each represent hydrogen, alkyl, alkoxyalkyl, alkylthioalkyl or halogenoalkyl or represent optionally substituted aryl, or $R^3$ and $R^4$ together represent a divalent alkylene radical, $R^5$ represents hydrogen or alkyl and Ar represents optionally substituted phenyl, or represents optionally substituted pyridyl U.S. Pat. No. 4,770,692 discloses the following 4-cyano-(nitro)-5-oxy(thio)pyrazole derivatives, compositions containing them, and herbicidal and plant growth regulating methods of using them:

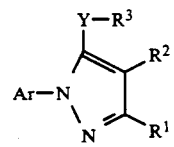

in which $R^1$ represents hydrogen, alkyl or halogenoalkyl, $R^2$ represents nitro or cyano, $R^3$ represents optionally substituted alkyl, optionally substituted alkenyl, optionally substituted alkynyl, optionally substituted cycloalkyl, optionally substituted cycloalkylalkyl, optionally substituted aralkyl or optionally substituted aryl, Ar represents phenyl which is substituted twice or more, or optionally substituted pyridyl, and Y represents O, S, SO or SO$_2$.

U.S. Pat. No. 4,770,693 claims the following 5-acylamino-1-phenylpyrazoles, compositions containing them, and herbicidal method of using them:

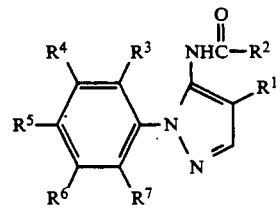

in which $R^1$ represents cyano, alkoxycarbonyl, alkenyloxycarbonyl, alkynyloxycarbonyl, aminocarbonyl, alkylaminocarbonyl, alkenylaminocarbonyl or alkynylaminocarbonyl, $R^2$ represents hydrogen, alkyl, alkenyl, alkynyl, optionally substituted cycloalkyl, alkoxyalkyl, alkylthioalkyl, halogenoalkyl or optionally substituted aryl and $R^3$, $R^4$, $R^5$, $R^6$ and $R^7$, which are identical or different, represent hydrogen, halogen, cyano, nitro, alkyl, alkoxy, alkylsulfonyl, alkoxycarbonyl or a radical —$R^8$;

wherein $R^8$ represents halogenoalkyl, with the proviso that at least one of the radicals $R^3$, $R^4$, $R^5$, $R^6$ or $R^7$ represents a radical —$R^8$, but $R^1$ does not represent cyano if $R^5$ represents trifluoromethyl.

U.S. Pat. No. 4,770,688 claims the following 5-azido or 5-phosphorimido-1-arylpyrazoles, compositions containing them, and herbicidal and plant growth regulating methods of using them:

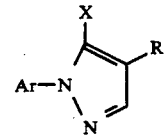

in which R represents cyano or nitro,

Ar represents in each case optionally substituted phenyl or pyridyl,

X represents an azido group, or represents the radical

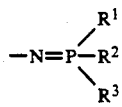

and

R¹, R² and R³ each independently represents alkyl, alkenyl, alkynyl, halogenoalkyl, alkoxy, alkoxyalkyl, cycloalkyl or cycloalkyloxy, or represents in each case optionally substituted aryl, aryloxy, aralkyl or aralkyloxy;

but wherein, in the case where R represents cyano and X simultaneously represents an azido group, Ar does not represent unsubstituted phenyl and does not represent 5-nitro-2-pyridyl.

U.S. Pat. No. 4,772,312 claims the following 5-amino-1-pyridylpyrazoles, compositions containing them, and herbicidal method of using them:

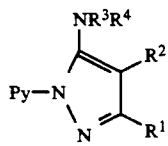

in which R¹ represents hydrogen or represents alkyl with 1 to 12 carbon atoms,

R² represents hydrogen, nitro, nitroso or halogen, or represents a radical —C(O)—R⁵, wherein R⁵ represents hydrogen, hydroxyl, alkyl, alkenyl, alkynyl, halogenoalkyl, alkoxyalkyl or alkylthioalkyl, or optionally substituted cycloalkyl, or optionally substituted aryl, or represents alkoxy or alkylthio, or optionally substituted aryloxy, or optionally substituted arylthio, alkylamino or dialkylamino, or optionally substituted arylamino, R³ represents hydrogen, or a radical —C(X)—R⁶, or a radical —S(O)n—R⁷, R⁴ represents hydrogen, or alkyl, or a radical —C(X)—R⁶, or a radical —S(O)n—R⁷, and in the case where R³ represents an —SO₂—R⁷ radical, also represents an inorganic or organic cation bonded in salt form, and R⁶ represents hydrogen, alkyl, alkenyl, alkynyl, halogenoalkyl, alkoxyalkyl or alkylthioalkyl, or optionally substituted cycloalkyl, or optionally substituted aryl, or alkoxy or alkylthio, or optionally substituted aryloxy, or optionally substituted arylthio, or alkylamino or dialkylamino, or optionally substituted arylamino, X represents oxygen or sulphur, n represents the number 0, 1 or 2;

R⁷ represents alkyl, halogenalkyl or optionally substituted aryl; and

Py represents substituted C-linked pyridyl.

U.S. Pat. No. 4,787,930 claims the following 5-amino-1-phenylpyrazole herbicides and plant growth regulators:

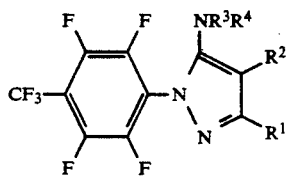

in which R¹ represents hydrogen, or alkyl of 1 to 12 carbon atoms;

R² represents hydrogen, nitro, nitroso, or hydrogen or —C(=O)R⁵;

R³ represents hydrogen, —C(=X)R⁶, or —S(O)n—R⁷; and

R⁴ represents hydrogen, alkyl, —C(=X)R⁶, or —S-(O)n—R⁷, or in the case where R³ represents a —SO₂—R⁷ radical or a —CO—CmF₂m+₁ radical, also represents an inorganic or organic cation bonded in salt form.

U.S. Pat. No. 4,435,208 claims the following herbicidally active substituted phenoxycinnamic acid derivatives:

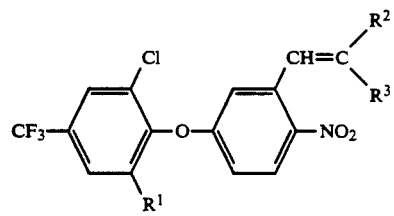

in which R¹ represents a hydrogen or chlorine atom;

R² represents a hydrogen atom, a cyano group, an optionally substituted radical selected from alkyl, aryl, alkanoyl, benzoyl, alkoxycarbonyl, alkenoxycarbonyl, alkynoxycarbonyl, aralkoxycarbonyl and aryloxycarbonyl, or a radical of the general formula —COOM, in which M represents a hydrogen atom, one equivalent of an alkali metal ion or alkaline earth metal ion or optionally substituted ammonium, and R³ represents a cyano group or a radical of the general formula —CO—[Y—(CR⁴R⁵)—CO)n—Z;

wherein Y represents an oxygen or sulfur atom or an imino (NH) or alkylimino (N-alkyl) group, R⁴ and R⁵ independently or each other represent a hydrogen atom or a methyl group, n is 0 or 1; and Z represents an optionally substituted radical.

DETAILED DESCRIPTION OF THE INVENTION

It has now been discovered that b-pyrazolylacrylic acid derivatives of the following structure are highly active herbicides:

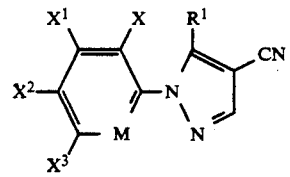

wherein X is chlorine or fluorine, X¹ is hydrogen, chlorine, or fluorine, X² is chlorine, fluorine, trifluoromethyl, or ethoxy, and X³ is hydrogen, chlorine, or fluorine, or when M is —CH—, —CF—, —CCl—, or —N—; and R¹ is —CH=C(—R²)—C(=O)—Z—[S-(O)₂]n—R³ wherein R² is hydrogen or methyl; Z is —O—, —S—, or —NR⁴—; and n is 0 or 1;

when Z is —O— or —S— and n is O, R³ is selected from the group consisting of hydrogen, sodium, lower alkyl, cyanomethyl, propargyl, isopropylideneamino, dihydrofuran-2(3H)-one-3-yl, phenylmethyl optionally substituted in the 4-position with methylthio, and —R-

5—$COR^6$, where $R^5$ is a divalent alkylene of 1 to 3 carbons and $R^6$ is hydrogen, amino, dimethylamino, methylsulfonylamino, or an alkoxy of 1 to 4 carbons;

when Z is —$NR^4$— and n is 0, $R^3$ is selected from the group consisting of hydrogen, lower alkyl, methoxy, 1-cyano-1-methylethyl, ethoxycarbonylmethyl, phenylmethyl, and phenyl; and $R^4$ is hydrogen, methyl, or taken with $R^3$ —$C_2H_5OC_2H_5$— to form a morpholine ring;

when Z is —$NR^4$— and n is 1, $R^3$ is selected from the group consisting of lower alkyl, trifluoromethyl, cyclohexylmethyl, 2-phenylethyl, 2-phenylethenyl, amino, d-10-camphoryl, 3,5-dimethylisoxazol-4-yl, phenylmethyl optionally substituted with one or more of chlorine, bromine, fluorine, or methyl, and phenyl optionally substituted with chlorine or methyl; and $R^4$ is hydrogen; in addition when $R^2$ is hydrogen and $R^3$ is lower alkyl or phenylmethyl, $R^4$ may be sodium.

Lower alkyl means a straight or branched chain of 1 to 4 carbon atoms.

Preferred compounds are those
wherein X is chlorine, $X^1$ is hydrogen or chlorine, $X^2$ is chlorine or trifluoromethyl, and $X^3$ is hydrogen, M is —CH— or —N—, and Z is —O— or —$NR^4$—;

when Z is —O— and n is 0, $R^3$ is selected from the group consisting of hydrogen, sodium, methyl, ethyl, phenylmethyl, and —$R^5$—$COR^6$ in which $R^6$ is hydroxy or an alkoxy of 1 to 4 carbons;

when Z is —$NR^4$— and n is 0, $R^3$ is selected from the group consisting of hydrogen, lower alkyl, ethoxycarbonylmethyl, phenylmethyl, and phenyl; and $R^4$ is hydrogen, methyl, or taken with $R^3$ —$C_2H_5OC_2H_5$— to form a morpholine ring;

Z is —$NR^4$— and n is 1, $R^3$ is selected from the group consisting of lower alkyl of 1 to 4 carbon atoms, or phenylmethyl optionally substituted with one or two of chlorine or methyl; and $R^4$ is hydrogen; in addition when $R^2$ is hydrogen, and $R^3$ is methyl, 1-methylethyl, or phenylmethyl, $R^4$ may also be sodium.

Particularly preferred compounds are those
wherein X is chlorine, $X^1$ is hydrogen or chlorine, $X^2$ is chlorine or trifluoromethyl, and $X^3$ is hydrogen, M is —N—, and Z is —O— or —$NR^4$—; when Z is —O— and n is 0, $R^3$ is selected from the group consisting of hydrogen, sodium, methyl, ethyl, carboxymethyl, 1-carboxyethyl, methoxycarbonylmethyl, ethoxycarbonylmethyl, 1,1-dimethylethoxycarbonylmethyl, 1-(methoxycarbonyl)ethyl, 1-(1,1-dimethylethoxyoarbonyl)ethyl, and phenylmethyl;

when Z is —$NR^4$— and n is 0, $R^3$ is selected from the group consisting of hydrogen, methyl, and 1-methylpropyl; and $R^4$ is hydrogen or methyl;

when Z is —$NR^4$— and n is 1, $R^3$ is selected from the group consisting of lower alkyl or phenylmethyl; and $R^4$ is hydrogen; in addition when $R^2$ is hydrogen, and $R^3$ is methyl, 1-methylethyl, or phenylmethyl, $R^4$ may also be sodium.

The compounds of the present invention were prepared by methods known to those of ordinary skill in the art.

The 5-amino-4-cyano-1-(substituted-phenyl)-1H-pyrazoles and 5-amino-4-cyano-1-(substituted-pyridin-2-yl)-1H-pyrazoles) used as intermediates in preparing the compounds of the present invention are known and are disclosed as herbicides in U.S. Pat. No. 4,496,390.

The 5-amino-4-substituted-1-aryl-1H-pyrazole intermediates were converted to the corresponding diazonium salts with tert-butyl nitrite. The diazonium salts were then subjected to a modified Meerwein reaction, as described by M. P. Doyle et al., J.Org. Chem., 42, 14, 2431 (1977), with a lower alkyl acrylate and copper(II) chloride in acetonitrile, affording the corresponding lower alkyl 2-chloro-3-[4-substituted-1-aryl-1H-pyrazol-5-yl]propionates. The lower alkyl propionates were then dehydrohalogenated with sodium hydride in dimethylformamide, yielding the corresponding lower alkyl 3-[4-substituted-1-aryl-1H-pyrazol-5-yl]acrylates, as exemplified in Example 1 below.

Alternatively, the lower alkyl propionates were dehydrohalogenated with potassium carbonate in 50% aqueous ethanol and then hydrolyzed with concentrated hydrochloric acid, yielding the corresponding 3-[4-substituted-1-aryl-1H-pyrazol-5-yl]acrylic acids, as exemplified in Example 2 below. The acrylic acids were optionally converted to their acid chlorides, which were in turn reacted with various alcohols, thiols, amines, and sulfonamides by well-known procedures, yielding the corresponding acrylic acid derivatives of the present invention. These procedures are shown in Examples 7-11 below.

The acrylic acids were also reacted with an appropriately substituted halogen intermediate under basic conditions in a solvent, for example, acetone, yielding the corresponding acrylic acid esters. This type of chemistry was usually employed to produce complex acid esters, for example, in which $R^3$ is 1,1-dimethylethoxycarbonylmethyl, as in Example 12 below. The complex esters were optionally hydrolyzed with trifluoroacetic acid, yielding a complex acid, for example, in which $R^3$ is carboxymethyl, as in Example 13 below.

An alternative route to compounds of the invention, bypassing the 5-amino-1-aryl-4-cyano-1H-pyrazole intermediates, is exemplified in Example 5 below.

EXAMPLE 1

Synthesis of Ethyl
3-[4-Cyano-1-(2,3,4-Trichlorophenyl)-1H-Pyrazol-5-Yl]Acrylate (Compound 6)

Step A: Ethyl 2-chloro-3-[4-cyano-1-(2,3,4-trichlorophenyl)-1H-pyrazol-5-yl]propionate To a stirred solution of 1.6 grams (0.015 mole) of tert-butyl nitrite in 20 mL of ethyl acrylate and 20 mL of acetonitrile was added 1.2 grams (0.012 mole) of copper(II) chloride. Upon completion of addition, the reaction mixture was stirred for five minutes, and then 2.9 grams (0.01 mole) of 5-amino-4-cyano-1-(2,3,4-trichlorophenyl)-1H-pyrazole was added in portions. Upon completion of the addition, the reaction mixture was stirred for 2.75 hours at a temperature of about 27° C. After this time, the reaction mixture was poured into 150 mL of aqueous 20% hydrochloric acid, where it was stirred for 10 minutes. The two-phase mixture was extracted with methylene chloride. After the extract had been standing for a few minutes, an oily solid separated out. This solid was collected by filtration, and nmr analysis showed that it was not the proposed product. The methylene chloride filtrate was washed with aqueous 20% hydrochloric acid and then with water. The organic layer was dried with magnesium sulfate and filtered. The filtrate was concentrated under reduced pressure, yielding 3.6 grams of crude, oily product. A 2.0 gram sample of the crude product was subjected to column chromatography on silica gel with 1:1 heptane/ethyl acetate eluent. Those fractions found by thin layer chromatography to contain a major constituent other than eluent and starting materials were combined and concentrated under reduced pressure, yielding 0.9 gram of ethyl 2-chloro-3-[4-cyano-1-(2,3,4-trichlorophenyl)-1H-pyrazol-5-yl]propionate. The nmr spectrum was consistent with the proposed structure.

Step B: Ethyl 3-[4-cyano-1-(2,3,4-trichlorophenyl)-1H-pyrazol-5-yl]acrylate

To a stirred, slightly warmed solution of 1.4 grams (0.003 mole) of ethyl 2-chloro-3-[4-cyano-1-(2,3,4-trichlorophenyl)-1H-pyrazol-5-yl]propionate in 25 mL of N,N-dimethylformamide was added in one portion 0.1 gram (0.004 mole) of sodium hydride. Upon completion of the addition the reaction mixture was warmed to about 60° C., where it was stirred for 1.75 hours. The reaction mixture was then allowed to cool to ambient temperature, where it was stirred for about 18 hours. The reaction mixture was again warmed to about 60° C., where it was stirred for two hours. The reaction mixture was cooled and concentrated under reduced pressure. The residue remaining was stirred with water for about 40 minutes, giving a solid that was collected by filtration. The solid was recrystallized from ethanol and water, yielding 0.6 gram of ethyl 3-[4-cyano-1-(2,3,4-trichlorophenyl)-1H-pyrazol-5-yl]acrylate, m.p. 131°-134° C. The nmr spectrum was consistent with the proposed structure.

EXAMPLE 2

Synthesis of 3-[4-Cyano-1-(2,3,4-Trichlorophenyl)-1H-Pyrazol-5-Yl]Acrylic Acid (Compound 4)

A stirred slurry of 0.35 gram (0.0009 mole) of ethyl 2-chloro-3-[4-cyano-1-(2,3,4-trichlorophenyl)-1H-pyrazol-5-yl]propionate and 0.24 gram (0.002 mole) of potassium carbonate in 35 mL of 50% aqueous ethanol was heated at reflux for one hour. The reaction mixture was then cooled and concentrated under reduced pressure, leaving a residue. The residue was dissolved in water, and the solution was washed once with methylene chloride. The aqueous layer was stirred and acidified by the dropwise addition of concentrated hydrochloric acid. Upon acidification, the mixture was stirred for one hour, and the resultant solid was collected by filtration. The solid was dried, yielding 0.21 gram of 3-[4-cyano-1-(2,3,4-trichlorophenyl)-1H-pyrazol-5-yl]acrylic acid; m.p. 215°-219° C. A small sample was recrystallized from ethanol and water to raise the m.p. to 226.5°-228.5° C. The nmr spectrum was consistent with the proposed structure.

EXAMPLE 3

Synthesis of Methyl 3-[4—Cyano-1-(3-Chloro-5-trifluoromethylpyridin-2-Yl)-1H-Pyrazol-5-Yl]Acrylate (Compound 16)

Step A: Methyl 2-chloro-3-[4-cyano-1-(3-chloro-5-trifluoromethylpyridin-2-yl)-1H-pyrazol-5yl]propionate This compound was prepared in a manner analogous to that of Example 1, Step A, using 5.8 grams (0.020 mole) of 5-amino-4-cyano-1-(3-chloro-5-trifluoromethylpyridin-2-yl)-1H-pyrazole, 3.1 grams (0.030 mole) of tert-butyl nitrite, 3.2 grams (0.024 mole) of copper(II) chloride, and 40 mL of methyl acrylate in 40 mL of acetonitrile. The yield of methyl 2-chloro-3-[4-cyano-1-(3-chloro-5-trifluoromethylpyridin-2-yl)-1H-pyrazol-5-yl]propionate was 7.2 grams. The nmr spectrum was consistent with the proposed structure.

Step B: Methyl 3-[4-cyano-1-(3-chloro-5-trifluoromethylpyridin-2-yl)-1H-pyrazol-5-yl]acrylate This compound was prepared in a manner analogous to that of Example 1, Step B, using 1.S grams (0.004 mole) of methyl 2-chloro-3-[4-cyano-1-(3-chloro-5-trifluoromethylpyridin-2-yl)-1H-pyrazol-5-yl]propionate and 0.12 gram (0.005 mole) of sodium hydride in 25 mL of N,N-dimethylformamide. The yield of methyl 3-[4-cyano-1-(3-chloro-5-trifluoromethylpyridin-2-yl)-1H-pyrazol-5-yl]acrylate was 0.3 gram, isolated as a waxy solid. The nmr spectrum was consistent with the proposed structure.

EXAMPLE 4

Synthesis of 3-[4-Cyano-1-(3-Chloro-5-TrifluoroMethylpyridin-2-Yl)-1H-Pyrazol-5-Yl]Acrylic Acid (Compound 14)

This compound was prepared in a manner analogous to that of Example 2, using 1.2 grams (0.003 mole) of methyl 2-chloro-3-[4-cyano-1-(3-chloro-5-trifluoromethylpyridin-2-yl)-1H-pyrazol-5-yl]propionate and 0.8 gram (0.006 mole) of potassium carbonate in 10 mL of water and 25 mL of ethanol. The yield of 3-[4-cyano-1-(3-chloro-5-trifluoromethylpyridin-2-yl)-1H-pyrazol-5-yl]acrylic acid was 0.6 gram; m.p. 225°-228° C. The nmr spectrum was consistent with the proposed structure.

EXAMPLE 5

Synthesis of 3-[4-Cyano-1-(3-Chloro-5-Trifluoromethylpyridin-2-Yl)-1H-Pyrazol-5-Yl]Acrylic Acid (Compound 14)

Step A: 4-Ethoxycarbonyl-5-methyl-1-(3-chloro-5-trifluoromethylpyridin-2-yl)-1H-pyrazole A stirred solution of 44.0 grams (0.21 mole) of 3-chloro-5-trifluoromethylpyridin-2-ylhydrazine and 38.6 grams (0.21 mole) of ethyl 2-acetyl-3-dimethylaminoacrylate, prepared by the method of J. R. Beck et al., J. Het. Chem., 24, 693 (1987), in 1000 mL of ethanol was heated at reflux for five hours. After this time, the reaction mixture was cooled to ambient temperature and concentrated under reduced pressure to a residual oil. The oil was taken up in methylene chloride and washed in succession with two 100 mL portions of aqueous 10% hydrochloric acid, an aqueous solution saturated with sodium bicarbonate, and water. The organic layer was dried and filtered. The filtrate was concentrated under reduced pressure, yielding 48.9 grams of 4-ethoxycarbonyl-5-methyl-1-(3-chloro-5-trifluoromethylpyridin-2-yl)-1H-pyrazole. The nmr spectrum was consistent with the proposed structure.

Step B: 4-Carboxy-5-methyl-1-(3-chloro-5-trifluoromethylpyridin-2-yl)-1H-pyrazole A stirred solution of 36.0 grams (0.11 mole) of 4-ethoxycarbonyl-5-methyl-1-(3-chloro-5-trifluoromethylpyridin-2-yl)-1H-pyrazole, prepared by the method of J. R. Beck et al., J. Het. Chem., 24, 693 (1987), and 53 mL of aqueous 10% sodium hydroxide in 145 mL of water and 390 mL of ethanol was heated at reflux for 30 minutes. After this time, the reaction mixture was concentrated under reduced pressure to a residue. The residue was poured into 600 mL of ice water. The mixture was acidified with concentrated hydrochloric acid, yielding a gummy solid. Small portions of the gummy solid were triturated with petroleum ether, yielding, when combined, 21.5 grams of solid 4-carboxy-5-methyl-1-(3-chloro-5-trifluoromethylpyridin-2-yl)-1H- pyrazole. The nmr spectrum was consistent with the proposed structure.

Step C: 4—Cyano-5-methyl-1-(3-chloro-5-trifluoromethylpyridin-2-yl)-1H-pyrazole

A stirred solution of 16.5 grams (0.054 mole) of 4-carboxy-5-methyl-1-(3-chloro-5-trifluoromethylpyridin-2-yl)-1H-pyrazole in 80 mL of thionyl chloride was heated at reflux for three hours. The reaction mixture was cooled and concentrated under reduced pressure, yielding the corresponding 4-carboxylic acid chloride. The acid chloride was taken up in 5 mL of tetramethylene sulfone, and 6.4 grams of sulfamide was added. The reaction mixture was heated, with stirring, at 120°–130° C. for one hour, after which the reaction mixture was poured into a solution consisting of 100 mL of aqueous 10% sodium hydroxide and 200 mL of water. The mixture was cooled, and a solid was collected by filtration. The solid was dissolved in methylene chloride, and the solution was dried with magnesium sulfate. The mixture was filtered and the filtrate was concentrated under reduced pressure, yielding 14.0 grams of 4-cyano-5-methyl-1-(3-chloro-5-trifluoromethylpyridin-1-yl)-1H-pyrazole. The nmr spectrum was consistent with the proposed structure.

Step D: 5-Bromomethyl-4-cyano-1-(3-chloro-5-trifluoromethylpyridin-2-yl)-1H-pyrazole To a stirred solution of 13.7 grams (0.05 mole) of 4-cyano-5-methyl-1-(3-chloro-5-trifluoromethylpyridin-2-yl)-1H-pyrazole in 140 mL of carbon tetrachloride was added 12.8 grams (0.07 mole) of N-bromosuccinimide. The reaction mixture was brought to reflux with illumination from a 150 watt lamp and maintained at reflux for 2.5 hours. The reaction mixture was cooled and then washed several times with an aqueous solution saturated with sodium chloride. The organic layer was dried with magnesium sulfate and filtered. The filtrate was concentrated under reduced pressure, yielding 14.6 grams of solid that was predominantly 5-bromomethyl-4-cyano-1-(3-chloro-5-trifluoromethylpyridin-2-yl)-1H-pyrazole. The nmr spectrum was consistent with the proposed structure.

Step E: 1-[[4—Cyano-1-(3-chloro-5-trifluoromethyl pyridin-2-yl)-1H-pyrazol-5-yl]methyl]pyridinium bromide A solution of 13.6 grams (0.044 mole) of 5-bromomethyl-4-cyano-1-(3-chloro-5-trifluoromethylpyridin-2-yl)-1H-pyrazole in 41 mL of pyridine was stirred at ambient temperature for three hours. After this time, the reaction mixture was slurried in 350 mL of diethyl ether and filtered. The filter cake was washed with additional diethyl ether. The filter cake was dried, yielding 11.9 grams of 1-[4-cyano-2-(3-chloro-5-trifluoromethylpyridin-2-yl)-1H-pyrazol-5-ylmethyl]-pyridinium bromide. The nmr spectrum was consistent with the proposed structure.

Step F: N-[4-(Dimethylamino)phenyl]-a-[4-cyano-1-(3-chloro-5-trifluoromethylpyridin-2-yl)-1H-pyrazol-5-yl]nitrone To a stirred suspension of 9.0 grams (0.020 mole) of 1-[[4-cyano-1-(3-chloro-5-trifluoromethylpyridin-2-yl)-1H-pyrazol-5-yl]methyl]pyridinium bromide and 3.5 grams (0.023 mole) of N,N-dimethyl-4-nitrosoaniline in 95 mL of ethanol was added a solution of 16 grams (0.12 mole) of potassium carbonate in 59 mL of water. When the addition was complete, the reaction mixture was stirred at ambient temperature for four hours. After this time, the reaction mixture was filtered. The filter cake was washed in succession with water, ethanol, and diethyl ether, yielding 7.6 grams of N-[4-(dimethylamino)phenyl]-a-[4-cyano-1-(3-chloro-5-trifluoromethylpyridin-2-yl)-1H-pyrazol-5-yl]nitrone.

The nmr spectrum was consistent with the proposed structure.

Step G: 4—Cyano-5-formyl-1-(3-chloro-5-trifluoromethylpyridin-2-yl)-1H-pyrazole

To a stirred suspension of 7.6 grams (0.02 mole) of N-[4-(dimethylamino)phenyl]-a-[4-cyano-1-(3-chloro-5-trifluoromethylpyridin-2-yl)-1H-pyrazol-5-yl]nitrone in 300 mL of ethyl acetate was added 400 mL of aqueous 6N hydrochloric acid, at which time all of the solid material dissolved. The aqueous layer was separated and extracted with one portion of ethyl acetate. An aqueous solution saturated with sodium chloride was added to the aqueous layer, and the mixture was extracted several more times with ethyl acetate. The ethyl acetate extracts were combined with the organic layer, and the combination was washed with water. The organic layer was dried with magnesium sulfate and filtered. The filtrate was concentrated under reduced pressure to a residual oil. The oil was cooled and triturated with heptane, yielding 2.5 grams of 4-cyano-5-formyl-1-(3-chloro-5-trifluoromethylpyridin-2-yl)-1H-pyrazole. The nmr spectrum was consistent with the proposed structure. (The compounds of Steps E, F, and G were prepared by the method of E. C. Taylor et al., J. Org. Chem., 43, 4, 736 (1978).)

Step H: 3-[5-Cyano-1-(3-chloro-5-trifluoromethylpyridin-2-yl)-1H-pyrazol-5-yl]acrylic acid A stirred solution of 0.3 grams (0.001 mole) of 4-cyano-5-formyl-2-(3-chloro-5-trifluoromethylpyridin-2-yl)-1H-pyrazole, 0.2 gram (0.002 mole) of malonic acid, two drops of piperidine, and 3 mL of pyridine was heated at reflux for about 18 hours. After this time, the reaction mixture was cooled and was concentrated under reduced pressure to a residue. The residue was stirred with excess aqueous 2N hydrochloric acid and ethyl acetate. The organic layer was separated and washed with aqueous 2N hydrochloric acid and then with water. The organic layer was dried with magnesium sulfate and filtered. The filtrate was concentrated under reduced pressure to a residue. The residue was triturated several times with petroleum ether, and each time the supernatent liquid was discarded. The resultant solid was dried, yielding 3-[4-cyano-2-(3-chloro-5-trifluoromethylpyridin-2-yl)-1H-pyrazol-5-yl]acrylic acid. The nmr spectrum was consistent with the proposed structure and was identical to the nmr spectrum of this compound prepared by the method of Example 4.

EXAMPLE 6

Synthesis of Methyl 3-[4-Cyano-1-(2,3,5,6-Tetrafluoro-4-Trifluoromethylphenyl)-1H-Pyrazol-5-Yl]Acrylate (Compound 9)

Step A: Methyl 2-chloro-3-[4-cyano-1-(2,3,5,6-tetrafluoro-4-trifluoromethylphenyl)-1H-pyrazol-5-yl]propionate This compound was prepared in a manner analogous to that of Example 1, Step A, with 4.0 grams of material that was about 50% (2.0 grams—0.006 mole) 5-amino-4-cyano-1-(2,3,5,6-tetrafluoro-4-trifluoromethylphenyl)-1H-pyrazole, 1.1 mL of tert-butyl nitrite, 0.7 gram of copper(II) chloride, and 13 mL of methyl acrylate in 13 mL of acetonitrile. The yield of methyl 2-chloro-3-[4-cyano-1-(2,3,5,6-tetrafluoro-4-trifluoromethylphenyl)-

1H-pyrazol-5-yl]propionate was 3.8 grams. The nmr spectrum was consistent with the proposed structure.

Step B: Methyl 3-[4-cyano-1-(2,3,5,6-tetrafluoro-4-trifluoromethylphenyl)-1H-pyrazol-5-yl]acrylate This compound was prepared in a manner analogous to that of Example 1, Step B, with 3.8 grams (0.009 mole) of methyl 2-chloro-3-[4-cyano-1-(2,3,5,6-tetrafluoro-4-trifluoromethylphenyl)-1H-pyrazol-5-yl]propionate, and 0.3 gram (0.012 mole) of sodium hydride in 70 ml of N,N-dimethylformamide. The yield of methyl 3-[4-cyano-1-(2,3,5,6-tetrafluoro-4-trifluoromethylphenyl)-1H-pyrazol-5-yl]acrylate was 1.7 grams. The nmr spectrum was consistent with the proposed structure.

EXAMPLE 7

Synthesis of 3-[4-Cyano-1-(3-Chloro-5-Trifluoromethylpyridin-2-yl)-1H-Pyrazol-5-Yl]Acrylamide (Compound 41)

Step A: 3-[4-Cyano-1-(3-chloro-5-trifluoromethylpyridin-2-yl)-1H-pyrazol-5-yl]acrylic acid chloride A stirred slurry of 1.1 grams (0.003 mole) of 3-[4-cyano-1-(3-chloro-5-trifluoromethylpyridin-2-yl)-1H-pyrazol-5-yl]acrylic acid and 1.0 mL of thionyl chloride in 20 mL of toluene was heated at about 72° C. for 25 minutes. The slurry was warmed to 98° C. over a 45 minutes period, during which time the reaction mixture became homogeneous. The reaction mixture was heated at 98° C. for 35 minutes. After this time, the reaction mixture was cooled and concentrated under reduced pressure, yielding 1.1 grams of 3-[4-cyano-1-(3-chloro-5-trifluoromethylpyridin-2-yl)-1H-pyrazol-5-yl]acrylic acid chloride. The acid chloride was used without purification.

Step B: 3-[4-Cyano-1-(3-chloro-5-trifluoromethylpyridin-2-yl)-1H-pyrazol-5-yl]acrylamide To a stirred, ice-cold solution of 10 mL (0.15 mole) of concentrated aqueous ammonia in 15 mL of tetrahydrofuran was added dropwise a solution of 0.35 gram (0.001 mole) of 3-[4-cyano-1-(3-chloro-5-trifluoromethylpyridin-2-yl)-1H-pyrazol-5-yl]acrylic acid chloride in 15 mL of tetrahydrofuran. Upon completion of the addition, the cooling bath was removed. The reaction vessel was closed by placing a rubber balloon over the open inlet of the reaction vessel. The reaction mixture was then allowed to warm to ambient temperature where it was stirred for one hour. After this time, the reaction mixture was concentrated at 45° C. under reduced pressure to a residual solid. The solid was triturated with petroleum ether and filtered, yielding a solid that did not completely melt at 212° C. The filtrate was concentrated in an air current, yielding a tan-yellow solid. Both solids were stirred in water separately. Each of the solids was then collected by filtration. The tan-yellow solid was triturated with two drops of isopropyl alcohol and petroleum ether. The suspension was cooled in a dry ice bath, and the solid was collected by filtration. The two solids were combined and dried, yielding 0.18 gram of 3-[4-cyano-1-(3-chloro-5-trifluoromethylpyridin-2-yl)-1H-pyrazol-5-yl]-acrylamide, m.p. 208°–210° C., dec. The nmr spectrum was consistent with the proposed structure.

EXAMPLE 8

Synthesis of N,N-Dimethyl-3-[4-Cyano-1-(3-Chloro-5-Trifluoromethylpyridin-2-Yl)-1H-Pyrazol-5-Yl]-Acrylamide (Compound 48)

To a stirred solution of 0.5 gram (0.001 mole) of 3-[4-cyano-1-(3-chloro-5-trifluoromethylpyridin-2-yl)-1H-pyrazol-5-yl]acrylic acid chloride and 1.3 grams (0.012 mole) of triethylamine in 100 mL of tetrahydrofuran was added 1.0 gram (0.012 mole) of dimethylamine hydrochloride. Upon completion of the addition, the reaction was stirred at ambient temperature for about 18 hours. The reaction mixture was then warmed to 65° C. where it was stirred for 15 minutes. The reaction mixture was cooled and concentrated under reduced pressure to a residue. The residue was dissolved in ethyl acetate, and the solution was washed with water. The organic layer was treated with decolorizing carbon and dried with magnesium sulfate. The mixture was filtered, and the filtrate was concentrated under reduced pressure to a residue. The residue was triturated with petroleum ether, and a solid was collected by filtration, yielding 0.2 gram of N,N-dimethyl-3-[4-cyano-1-(3-chloro-5-trifluoromethylpyridin-2-yl)-1H-pyrazol-5-yl]acrylamide; m.p. 116°–120° C. The nmr spectrum was consistent with the proposed structure.

EXAMPLE 9

Synthesis of Isopropylideneamino 3-[4-Cyano-1-(3-Chloro-5-Trifluoromethylpyridin-2-Yl)-1H-Pyrazol-5-Yl]Acrylate (Compound 28)

At 30° C. a solution of 0.6 gram (0.002 mole) of 3-[4-cyano-1-(3-chloro-5-trifluoromethylpyridin-2-yl)-1H-pyrazol-5-yl]acrylic acid chloride in 15 mL of tetrahydrofuran was added in portions to a stirred solution of 0.2 gram (0.002 mole) of acetone oxime, 0.3 gram (0.003 mole) of triethylamine, and a catalytic amount of 4-dimethylaminopyridine in 35 mL of toluene. Upon completion of the addition, the reaction mixture was stirred at 30° C. for five hours. After this time, the reaction mixture was diluted with water, and the pH was adjusted to about 3.0 with concentrated hydrochloric acid. The organic layer was separated and washed with an aqueous sodium chloride solution and then with water. The organic layer was concentrated under reduced pressure to a residual solid. The solid was subjected to column chromatography on silica gel with 1:1 hexane/ethyl acetate as eluant. Those fractions found by thin layer chromatography to contain a major constituent other than eluent and starting materials were combined and concentrated at 40° C. under reduced pressure, yielding 0.2 gram of isopropylideneamino 3-[4-cyano-1-(3-chloro-5-trifluoromethylpyridin-2-yl)-1H-pyrazol-5-yl]acrylate. The nmr spectrum was consistent with the proposed structure.

EXAMPLE 10

Synthesis of N-Phenylmethanesulfonyl-3-[4-Cyano-1-(3-Chloro-5-Trifluoromethylpyridin-2-Yl)-1H-Pyrazol-5-Yl]Yl]Acrylamide (Compound 67)

To a stirred solution of 0.31 gram (0.002 mole) of phenylmethanesulfonamide in 15 mL of tetrahydrofuran was added 0.05 gram (0.002 mole) of sodium hydride which was washed into the reaction vessel with 10 mL of tetrahydrofuran. The reaction mixture was warmed to reflux temperature, and a solution of 0.32 gram (0.001 mole) of 3-[4-cyano-1-(3-chloro-5-trifluoromethylpyridin-2-yl)-1H-pyrazol-5-yl]acrylic acid chloride in 5 mL of tetrahydrofuran was added dropwise during a 20 minute period. Upon completion of the addition, heating of the reaction mixture at reflux was continued for 75 minutes. After this time, the reaction mixture was cooled, and 1 mL of water was added. The mixture was concentrated under reduced pressure to a residue. The residue was dissolved in 35 mL of water, and the solution was acidified with aqueous 4N hydrochloric acid. The resultant solid was collected by filtration, and the filter cake was washed with water. The filter cake was then stirred with hot water. The hot water was decanted away from a semi-solid material. The semi-solid was stirred with fresh cold water which caused the semi-solid to totally solidify. The solid was collected by filtration and was then dissolved in 1:1 toluene/ethyl acetate. The solution was passed through a column of silica gel. The eluate was concentrated under reduced pressure, yielding 0.13 gram of N-phenylmethanesulfonyl-3-[4-cyano-1-(3-chloro-5-trifluoromethylpyridin-2-yl)-1H-pyrazol-5-yl]acrylamide. The nmr spectrum was consistent with the proposed structure.

EXAMPLE 11

Synthesis of Methoxycarbonylmethyl 3-[4-Cyano-1-(3-Chloro-5-Trifluoromethylpyridin-2-Yl)-1H-Pyrazol-5-Yl]Acrylate (Compound 30)

This compound was prepared in a manner analogous to that of Example 8, with 0.5 gram (0.0014 mole) of 3-[4-cyano- 1-(3-chloro-5-trifluoromethylpyridin-2-yl)-1H-pyrazol-5-yl]acrylic acid chloride, 0.2 gram (0.0017 mole) of methyl glycolate, and 0.2 gram (0.0020 mole) of triethylamine in 25 mL of tetrahydrofuran. The yield of methoxycarbonylmethyl 3-[4-cyano-1-(3-chloro-5-trifluoromethylpyridin-2-yl)-1H-pyrazol-5-yl]acrylate was 0.1 gram. The nmr spectrum was consistent with the proposed structure.

EXAMPLE 12

Synthesis of 1,1-Dimethylethoxycarbonylmethyl 3-[4-Cyano-1-(3-Chloro-5-Trifluoromethylpyridin-2-Yl)-1H-Pyrazol-5-Yl]Acrylate (Compound 33)

To a stirred solution of 0.4 gram (0.001 mole) of 3-[4-cyano-1-(3-chloro-5-trifluoromethylpyridin-2-yl)-1H-pyrazol-5-yl]acrylic acid in 25 mL of acetone were added in succession 0.2 gram (0.001 mole) of potassium carbonate and 0.2 gram (0.001 mole) of 1,1-dimethylethyl bromoacetate. Upon completion of the addition, the reaction mixture was stirred at 25° C. for 25 minutes, and then it was heated to reflux where it was stirred for one hour. After this time, the reaction mixture was cooled and concentrated under reduced pressure to a residue. The residue was shaken with methylene chloride and water. The organic layer was washed with water and then dried with calcium sulfate. The mixture was filtered through silica gel. The silica gel filter pad was washed with petroleum ether. The combined filtrates were concentrated under reduced pressure, yielding 0.5 gram of 1,1-dimethylethoxycarbonylmethyl 3-[4-cyano-1-(3-chloro-5-trifluoromethylpyridin-2-yl)-1H-pyrazol-5-yl]acrylate; m.p. 110°–112° C. The nmr spectrum was consistent with the proposed structure.

EXAMPLE 13

Synthesis of Carboxymethyl 3-[4-Cyano-1-(3-Chloro-5-Trifluoromethylpyridin-2-Yl)-1H-Pyrazol-5-Yl]Acrylate (Compound 29)

A solution of 0.33 gram (0.0007 mole) of 1,1-dimethylethoxycarbonylmethyl 3-[4-cyano-1-(3-chloro-5-trifluoromethylpyridin-2-yl)-1H-pyrazol-5-yl]acrylate in 1.3 mL of trifluoroacetic acid was stirred at ambient temperature for one hour. After this time, the reaction mixture was concentrated under reduced pressure at a temperature of about 30° to 50° C. The resultant residue was taken up in toluene, and the concentration procedure was repeated. The residue was shaken with diethyl ether and water and then concentrated under reduced pressure at a temperature of about 45° C., yielding 0.29 gram of 90% pure carboxymethyl 3-[4-cyano-1-(3-chloro-5-trifluoromethylpyridin-2-yl)-1H-pyrazol-5-yl]acrylate. The nmr spectrum was consistent with the proposed structure.

Representative compounds of the invention prepared by the methods exemplified above are shown in Table 1.

Characterizing properties of these compounds are given in Table 2.

HERBICIDAL ACTIVITY

The B-pyrazolylacrylic acids of this invention were tested in pre- and postemergence evaluations using a variety of broadleaf and grasseous crops and weeds. The test species used in demonstrating the herbicidal activity of this invention include cotton (*Gossypium hirsutum* var. DPL61) soybean (*Glycine max* var. Williams), field corn (*Zea mays* var. Agway 425X), rice (*Oryza sativa* var. Labelle), wheat (*Triticum aestivum* var. Wheaton), morningglory (*Ipomea lacunosa* or *Ipomea hederacea*), wild mustard (*Brassica kaber*), velvetleaf (*Abutilon theophrasti*), barnyardgrass (*Echinochloa crus-galli*), green foxtail (*Setaria viridis*), johnsongrass (*Sorghum halepense*), blackgrass (*Alopecurus myosuroides*), common chickweed (*Stellaria media*), and common cocklebur (*Xanthium pennsylvanicum*).

PREPARATION OF FLATS

Preemergence

Two disposable fiber flats (8 cm × 15 cm × 25 cm) for each rate of application for each candidate herbicide are filled to an approximate depth of 6.5 cm with steam-sterilized sandy loam soil. The soil is leveled and impressed with a template to provide five or six evenly spaced furrows 13 cm long and 0.5 cm deep in each flat.

In one case, seeds of cotton, soybean, corn, rice, and wheat are planted in the furrows of the first flat, and seeds of morningglory, wild mustard, velvetleaf, barnyardgrass, green foxtail, and johnsongrass are planted in the furrows of the second flat. The six-row template was employed to firmly press the seeds into place. A topping soil of equal portions of sand and sandy loam soil is placed uniformly on top of each flat to a depth of approximately 0.5 cm.

In another case, seeds of soybean, wheat, corn, green foxtail, and johnsongrass are planted in the furrows of the first flat, and seeds of velvetleaf, morningglory, common chickweed, cocklebur, and blackgrass are planted in the furrows of the second flat. The five-row template is employed to firmly press the seeds into place. A topping soil of equal portions of sand and sandy loam soil is placed uniformly on top of each flat to a depth of approximately 0.5 cm.

In each case, the flats are first watered, then sprayed with a solution of test compound as described below.

Postemergence

Two flats for each rate of application for each herbicide candidate are also prepared for postemergence application. The postemergence flats are prepared in the same manner as discussed above for the preemergence flats. The prepared flats are watered for 8–11 days, then the foliage of the emerged tests plants is sprayed with a solution of test compound as described below.

Application of Herbicides

In both the preemergence and postemergence tests, the candidate herbicides are applied as aqueous acetone solutions, usually at rates equivalent to 8.0 kilograms/hectare (kg/ha) and/or submultiples thereof, i.e., 4.0 kg/ha, 2.0 kg/ha, and so on.

The four flats (2 preemergence, 2 postemergence) are placed together and sprayed with 30 mL of test solution containing an appropriate amount of the test compound, i.e., approximately 7.5 mL of the test solution is sprayed on each of the four flats. Preemergence applications are made as sprays to the soil surface. Postemergence applications are made as sprays to the foliage. After treatment, the two preemergence flats are watered regularly at the soil surface for approximately 2 weeks, at which time phytotoxicity data are recorded. In the postemergence test the foliage is kept dry for 24 hours after treatment, then watered regularly for approximately 2 weeks, and phytotoxicity data recorded.

PREPARATION OF TEST SOLUTIONS

For flats of the size described above, an application rate of 8.0 kg/ha of active ingredient is equivalent to 0.06 g of active ingredient/flat (0.24 g for the four flats). A stock solution of 0.48 g of the candidate herbicide in 60 mL of a 50:50 mixture of water and acetone containing 0.5% (v/v) of sorbitan monolaurate emulsifier/solubilizer is divided into two 30 mL portions, each containing 0.24 g of the candidate herbicide. For the 8.0 kg/ha application, one of the 30 mL portions is sprayed undiluted onto the four flats (7.5 mL/flat). The remaining 30 mL portion of the stock solution is diluted with an additional 30 mL of the aqueous acetone/emulsifier mixture to provide 60 mL of a solution containing 0.24 g of candidate herbicide. As above, this solution is divided into two 30 mL portions, each containing 0.12 g of candidate herbicide. One of the 30 mL portions is applied, without further dilution, to the four flats for the 4.0 kg/ha rate. The remaining 30 mL portion is further diluted with an equal amount of aqueous acetone/emulsifier mixture, and the resulting 60 mL solution of 0.12 g candidate herbicide is divided into two 30 mL portions each containing 0.06 g of candidate herbicide. One of the 30 mL (0.06 g active) portions is used for the 2.0 kg/ha application rate and the other is used in the preparation of lower rate test solutions by the same serial dilution technique.

Phytotoxicity data are taken as percent control. Percent control is determined by a method similar to the 0 to 100 rating system disclosed in "Research Methods in Weed Science," 2nd ed., B. Truelove, Ed.; Southern Weed Science Society; Auburn University, Auburn, Ala., 1977. The rating system is as follows:

| Herbicide Rating System | | | |
|---|---|---|---|
| Rating Percent Control | Description of Main Categories | Crop Description | Weed Description |
| 0 | No effect | No crop reduction or injury | No weed control |
| 10 | | Slight discoloration or stunting | Very poor weed control |
| 20 | Slight effect | Some discoloration, stunting or stand loss | Poor weed control |
| 30 | | Crop injury more pronounced but not lasting | Poor to deficient weed control |
| 40 | | Moderate injury, crop usually recovers | Deficient weed control |
| 50 | Moderate effect | Crop injury more lasting, recovery doubtful | Deficient to moderate weed control |
| 60 | | Lasting crop injury, no recovery | Moderate weed control |
| 70 | | Heavy injury and stand loss | Control somewhat less than satisfactory |
| 80 | Severe | Crop nearly destroyed, a few survivors | Satisfactory to good weed control |
| 90 | | Only occasional live plants left | Very good to excellent control |
| 100 | Complete effect | Complete crop destruction | Complete weed destruction |

For herbicidal application, the active compounds are formulated into herbicidal compositions by admixture in herbicidally effective amounts with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These herbicidal compositions may be applied either as water-diluted sprays, or dusts, or granules to the areas in which suppression of vegetation is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and postemergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5–80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound, 17.9 parts of Palmetto clay, and 1.0 part of sodium lignosulfonate and 0.3 part of sulfonated aliphatic polyester as wetting agents. Frequently additional wetting agent and/or oil will be added to the tank mix for postemergence application to facilitate dispersion on the foliage and absorption by the plant.

Other useful formulations for herbicidal applications are emulsifiable concentrates (ECs) which are homogeneous liquid compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

Flowable formulations are similar to ECs except that the active ingredient is suspended in a liquid carrier, generally water. Flowables, like ECs, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agent, when used, normally comprises from 1 to 15% by weight of the composition.

Other useful formulations include suspensions of the active ingredient in a relatively non-volatile solvent such as water, corn oil, kerosene, propylene glycol, or other suitable solvents.

Still other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freon fluorinated hydrocarbons, may also be used. Water-soluble or water-dispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful herein with the present herbicidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed; the amount may be as low as, e.g. about 1 to 250 g/ha, preferably about 4 to 30 g/ha. For field use, where there are losses of herbicide, higher application rates (e.g., four times the rates mentioned above) may be employed.

The active herbicidal compounds of this invention may be used in combination with other herbicides, e.g. they may be mixed with, say, an equal or larger amount of a known herbicide such as chloroacetanilide herbicides such as 2-chloro-N-(2,6-diethylphenyl)-N-(methoxymethyl)acetamide (alachlor), 2-chloro-N-(2-ethyl-6-methylphenyl)-N-(2-methoxy-1-methylethyl)acetamide (metolachlor), and N-chloroacetyl-N-(2,6-diethylphenyl)glycine (diethatyl-ethyl); benzothiadiazinone herbicides such as 3-(1-methylethyl)-(1H)-2,1,3-benzothiadiazin-4-(3H)-one-2,2-dioxide (bentazon); triazine herbicides such as 6-chloro-N-ethyl-N-(1-methylethyl)1,3,5-triazine-2,4-diamine (atrazine), and 2-[4-chloro6-(ethylamino)-1,3,5-triazin-2-yl]amino-2-methylpropanenitrile (cyanazine); dinitroaniline herbicides such as 2,6-dinitro-N,N-dipropyl-4-(trifluoromethyl)benzeneamine (trifluralin); aryl urea herbicides such as N,-(3,4-dichlorophenyl)-N,N-dimethylurea (diuron) and N,N-dimethyl-N,-[3-(trifluoromethyl)phenyl]urea (fluometuron); and 2-[(2-chlorophenyl)methyl]-4,4-dimethyl-3-isoxazolidinone.

It is apparent that various modifications may be made in the formulation and application of the compounds of this invention without departing from the inventive concepts herein as defined in the claims.

TABLE 1

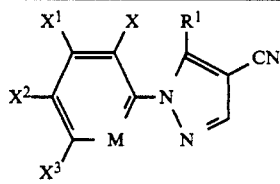

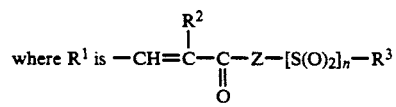

| Compound | X | X¹ | X² | X³ | M | R² | Z | n | R³ | R⁴ |
|---|---|---|---|---|---|---|---|---|---|---|
| 1 | Cl | H | CF$_3$ | H | CH | H | O | 0 | H | |
| 2 | Cl | H | CF$_3$ | H | CH | H | O | 0 | —CH$_3$ | |
| 3 | Cl | H | CF$_3$ | H | CH | H | O | 0 | —CH$_2$CO$_2$CH$_3$ | |
| 4 | Cl | Cl | Cl | H | CH | H | O | 0 | H | |
| 5 | Cl | Cl | Cl | H | CH | H | O | 0 | —CH$_3$ | |
| 6 | Cl | Cl | Cl | H | CH | H | O | 0 | —C$_2$H$_5$ | |
| 7 | Cl | Cl | Cl | H | CH | H | O | 0 | —CH$_2$CO$_2$CH$_3$ | |
| 8 | F | F | F | F | CF | H | O | 0 | —CH$_3$ | |
| 9 | F | F | CF$_3$ | F | CF | H | O | 0 | —CH$_3$ | |
| 10 | F | F | OC$_2$H$_5$ | F | CF | H | O | 0 | H | |
| 11 | F | F | OC$_2$H$_5$ | F | CF | H | O | 0 | —CH$_3$ | |
| 12 | Cl | H | Cl | H | N | H | O | 0 | H | |
| 13 | Cl | H | Cl | H | N | H | O | 0 | —CH$_3$ | |
| 14 | Cl | H | CF$_3$ | H | N | H | O | 0 | H | |
| 15 | Cl | H | CF$_3$ | H | N | H | O | 0 | Na$^+$ | |
| 16 | Cl | H | CF$_3$ | H | N | H | O | 0 | —CH$_3$ | |
| 17 | Cl | H | CF$_3$ | H | N | H | O | 0 | —C$_2$H$_5$ | |
| 18 | Cl | H | CF$_3$ | H | N | —CH$_3$ | O | 0 | —CH$_3$ | |
| 19 | Cl | H | CF$_3$ | Cl | N | H | O | 0 | —H | |
| 20 | Cl | H | —CF$_3$ | Cl | N | H | O | 0 | —CH$_3$ | |
| 21 | Cl | H | —CF$_3$ | —N(CH$_3$)CH$_2$C≡CH | N | H | O | 0 | H | |
| 22 | Cl | H | —CF$_3$ | —N(CH$_3$)CH$_2$C≡CH | N | H | O | 0 | —CH$_3$ | |
| 23 | Cl | H | —CF$_3$ | H | N | H | O | 0 | —CH$_2$C≡CH | |
| 24 | Cl | H | —CF$_3$ | H | N | H | O | 0 | —CH$_2$CN | |
| 25 | Cl | H | —CF$_3$ | H | N | H | O | 0 | ![lactone structure] | |
| 26 | Cl | H | —CF$_3$ | H | N | H | O | 0 | —CH$_2$φ | |
| 27 | Cl | H | —CF$_3$ | H | N | H | O | 0 | —CH$_2$φ, 4-SCH$_3$ | |
| 28 | Cl | H | —CF$_3$ | H | N | H | O | 0 | N=C(CH$_3$)$_2$ | |
| 29 | Cl | H | —CF$_3$ | H | N | H | O | 0 | —CH$_2$CO$_2$H | |
| 30 | Cl | H | —CF$_3$ | H | N | H | O | 0 | —CH$_2$CO$_2$CH$_3$ | |
| 31 | Cl | H | CF$_3$ | H | N | H | S | 0 | —CH$_2$CO$_2$CH$_3$ | |
| 32 | Cl | H | —CF$_3$ | H | N | H | O | 0 | —CH$_2$CO$_2$C$_2$H$_5$ | |
| 33 | Cl | H | —CF$_3$ | H | N | H | O | 0 | —CH$_2$CO$_2$C(CH$_3$)$_3$ | |
| 34 | Cl | H | —CF$_3$ | H | N | H | O | 0 | —CH(CH$_3$)CO$_2$H | |
| 35 | Cl | H | —CF$_3$ | H | N | H | O | 0 | —CH(CH$_3$)CO$_2$CH$_3$ | |
| 36 | Cl | H | —CF$_3$ | H | N | H | O | 0 | —CH(CH$_3$)CO$_2$C(CH$_3$)$_3$ | |
| 37 | Cl | H | —CF$_3$ | H | N | H | O | 0 | —CH$_2$C(O)NH$_2$ | |
| 38 | Cl | H | —CF$_3$ | H | N | H | O | 0 | —CH(CH$_3$)C(O)NH$_2$ | |
| 39 | Cl | H | —CF$_3$ | H | N | H | O | 0 | —CH(CH$_3$)C(O)N(CH$_3$)$_2$ | |
| 40 | Cl | H | —CF$_3$ | H | N | H | O | 0 | —CH(CH$_3$)C(O)NHS(O)$_2$CH$_3$ | |
| 41 | Cl | H | —CF$_3$ | H | N | H | —NR⁴— | 0 | H | H |
| 42 | Cl | H | —CF$_3$ | H | N | H | —NR⁴— | 0 | CH$_3$ | H |
| 43 | Cl | H | —CF$_3$ | H | N | H | —NR⁴— | 0 | —CH(CH$_3$)C$_2$H$_5$ | H |
| 44 | Cl | H | —CF$_3$ | H | N | H | —NR⁴— | 0 | —CH$_2$CO$_2$C$_2$H$_5$ | H |
| 45 | Cl | H | —CF$_3$ | H | N | H | —NR⁴— | 0 | —C(CH$_3$)$_2$C≡N | H |
| 46 | Cl | H | —CF$_3$ | H | N | H | —NR⁴— | 0 | φ | H |
| 47 | Cl | H | —CF$_3$ | H | N | H | —NR⁴— | 0 | CH$_2$φ | H |
| 48 | Cl | H | —CF$_3$ | H | N | H | —NR⁴— | 0 | —CH$_3$ | —CH$_3$ |
| 49 | Cl | H | —CF$_3$ | H | N | H | —NR⁴— | 0 | —OCH$_3$ | —CH$_3$ |
| 50 | Cl | H | —CF$_3$ | H | N | H | —NR⁴— | 0 | —CH$_2$CH$_2$OCH$_2$CH$_2$— | |
| 51 | Cl | H | —CF$_3$ | H | —CH | H | —NR⁴— | 1 | —CH$_2$φ | H |
| 52 | Cl | Cl | Cl | H | —CH | H | —NR⁴— | 1 | —CH$_2$φ | H |
| 53 | Cl | H | —CF$_3$ | H | N | H | —NR⁴— | 1 | —CH$_3$ | H |
| 54 | Cl | H | —CF$_3$ | H | N | H | —NR⁴— | 1 | —CH$_3$ | Na$^+$ |
| 55 | Cl | H | —CF$_3$ | H | N | H | —NR⁴— | 1 | —C$_2$H$_5$ | H |
| 56 | Cl | H | —CF$_3$ | H | N | H | —NR⁴— | 1 | —C$_3$H$_7$ | H |
| 57 | Cl | H | —CF$_3$ | H | N | H | —NR⁴— | 1 | —CH(CH$_3$)$_2$ | H |
| 58 | Cl | H | —CF$_3$ | H | N | H | —NR⁴— | 1 | —CH(CH$_3$)$_2$ | Na$^+$ |
| 59 | Cl | H | —CF$_3$ | H | N | H | —NR⁴— | 1 | —CH$_2$CH(CH$_3$)$_2$ | H |

TABLE 1-continued

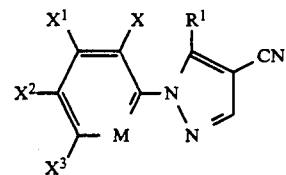

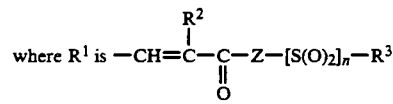

| Compound | X | X¹ | X² | X³ | M | R² | Z | n | R³ | R⁴ |
|---|---|---|---|---|---|---|---|---|---|---|
| 60 | Cl | H | —CF₃ | H | N | H | —NR⁴— | 1 | —CH(CH₃)C₂H₅ | H |
| 61 | Cl | H | —CF₃ | H | N | H | —NR⁴— | 1 | —CH₂-cyclohexyl | H |
| 62 | Cl | H | —CF₃ | H | N | H | —NR⁴— | 1 | —CF₃ | H |
| 63 | Cl | H | —CF₃ | H | N | H | —NR⁴— | 1 | —NH₂ | H |
| 64 | Cl | H | —CF₃ | H | N | H | —NR⁴— | 1 | φ | H |
| 65 | Cl | H | —CF₃ | H | N | H | —NR⁴— | 1 | φ, 2-Cl | H |
| 66 | Cl | H | —CF₃ | H | N | H | —NR⁴— | 1 | φ, 4-CH₃ | H |
| 67 | Cl | H | —CF₃ | H | N | H | —NR⁴— | 1 | —CH₂φ | H |
| 68 | Cl | H | —CF₃ | H | N | H | —NR⁴— | 1 | —CH₂φ | Na⁺ |
| 69 | Cl | H | —CF₃ | H | N | H | —NR⁴— | 1 | —CH₂φ, 2-Cl | H |
| 70 | Cl | H | —CF₃ | H | N | H | —NR⁴— | 1 | —CH₂φ, 3-Cl | H |
| 71 | Cl | H | —CF₃ | H | N | H | —NR⁴— | 1 | —CH₂φ, 4-Cl | H |
| 72 | Cl | H | —CF₃ | H | N | H | —NR⁴— | 1 | —CH₂φ, 2-F | H |
| 73 | Cl | H | —CF₃ | H | N | H | —NR⁴— | 1 | —CH₂φ, 2-Br | H |
| 74 | Cl | H | —CF₃ | H | N | H | —NR⁴— | 1 | —CH₂φ, 2,4-Cl₂ | H |
| 75 | Cl | H | —CF₃ | H | N | H | —NR⁴— | 1 | —CH₂φ, 3-CH₃ | H |
| 76 | Cl | H | —CF₃ | H | N | H | —NR⁴— | 1 | —CH₂φ, 4-CH₃ | H |
| 77 | Cl | H | —CF₃ | H | N | H | —NR⁴— | 1 | —CH₂CH₂φ | H |
| 78 | Cl | H | —CF₃ | H | N | H | —NR⁴— | 1 | —CH=CHφ | H |
| 79 | Cl | H | —CF₃ | H | N | H | —NR⁴— | 1 | —CH₂-(bicyclic ketone) | H |
| 80 | Cl | H | —CF₃ | H | N | H | —NR⁴— | 1 | 3,5-dimethylisoxazol-4-yl | H |

TABLE 2

Characterizing Properties

| Compound No. | M.P. (°C.) |
|---|---|
| 1 | 74–177 |
| 2 | 113–114 |
| 3 | clear oil |
| 4 | 226.5–228.5 |
| 5 | 180.5–181.5 |
| 6 | 131–134 |
| 7 | solid |
| 8 | solid |
| 9 | viscous oil |
| 10 | waxy solid |
| 11 | oil |
| 12 | 217–219 |
| 13 | 116.5–168 |
| 14 | 225–228 |
| 15 | solid |
| 16 | waxy solid |
| 17 | 98–101 |
| 18 | solid |
| 19 | solid |
| 20 | solid |
| 21 | solid |
| 22 | 115–117.5 |
| 23 | glassy material |
| 24 | oil |
| 25 | 166–168 |
| 26 | 97–99.5 |
| 27 | solid |
| 28 | solid |
| 29 | foamy solid |
| 30 | oil |

TABLE 2-continued

Characterizing Properties

| Compound No. | M.P. (°C.) |
|---|---|
| 31 | oil |
| 32 | viscous oil |
| 33 | 110–112 |
| 34 | solid |
| 35 | viscous fluid |
| 36 | 120–122 |
| 37 | solid |
| 38 | solid |
| 39 | solid |
| 40 | solid |
| 41 | 208–210; dec. |
| 42 | 208.5–210 |
| 43 | 146–148 |
| 44 | viscous liquid |
| 45 | 194–197 |
| 46 | 204–207 |
| 47 | 125–129 |
| 48 | 116–120 |
| 49 | solid |
| 50 | 146–149; dec |
| 51 | solid |
| 52 | solid |
| 53 | solid |
| 54 | solid |
| 55 | 158–162 |
| 56 | solid |
| 57 | solid |
| 58 | solid |
| 59 | solid |
| 60 | solid |
| 61 | 100; dec |
| 62 | 168–170 |
| 63 | solid |
| 64 | 158–160; dec |
| 65 | solid |
| 66 | solid |
| 67 | solid |
| 68 | solid |
| 69 | solid |
| 70 | solid |
| 71 | solid |
| 72 | solid |
| 73 | solid |
| 74 | solid |
| 75 | solid |
| 76 | solid |
| 77 | solid |
| 78 | solid |
| 79 | 102–106 |
| 80 | solid |

TABLE 3

PREEMERGENCE HERBICIDAL ACTIVITY (% Control)

| Compound No. | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| Rate (kg/ha) | 0.5 | 0.5 | 0.5 | 1.0 | 0.5 | 1.0 | 0.5 | 0.5 | 0.5 | 0.5 | 0.5 | 1.0 | 1.0 | 1.0 | 1.0 | 1.0 |
| Cotton | 40 | 80 | 20 | 20 | 70 | 40 | 70 | 0 | 30 | 70 | 30 | 10 | 5 | 90 | 90 | 90 |
| Soybean | 95 | 100 | 95 | 50 | 15 | 5 | 10 | 0 | 0 | 0 | 30 | 95 | 15 | 100 | 100 | 100 |
| Corn | 95 | 90 | 85 | 60 | 15 | 5 | 70 | 20 | 50 | 70 | 50 | 85 | 80 | 100 | 100 | 100 |
| Rice | 80 | 70 | 20 | 60 | 15 | 10 | 40 | 10 | 50 | 15 | 10 | 10 | 5 | 60 | 85 | 95 |
| Wheat | 95 | 9 | 90 | 70 | 15 | 50 | 70 | 0 | 10 | 0 | 0 | 20 | 20 | 90 | 95 | 95 |
| Morningglory | 95 | 100 | 100 | 80 | 85 | 100 | 80 | 30 | 70 | 80 | 80 | 60 | 20 | 100 | 95 | 100 |
| Wild mustard | 100 | 100 | 100 | 100 | 70 | 100 | 100 | 0 | 100 | 70 | 50 | 85 | 95 | 100 | 100 | 100 |
| Velvetleaf | 100 | 100 | 100 | 95 | 90 | 100 | 90 | 5 | 100 | 100 | 100 | 80 | 20 | 100 | 90 | 100 |
| Barnyardgrass | 70 | 90 | 70 | 5 | 20 | 90 | 85 | 70 | 70 | 15 | 40 | 85 | 60 | 90 | 95 | 100 |
| Green foxtail | 30 | 95 | 20 | 80 | 30 | 100 | 30 | 70 | 100 | 0 | 0 | 10 | 50 | 100 | 100 | 100 |
| Johnsongrass | 85 | 95 | 100 | 85 | 85 | 90 | 95 | 0 | 90 | 70 | 50 | 95 | 90 | 100 | 100 | 100 |

| Compound No. | 17 | 18 | 19 | 20 | 21 | 22 | 23 | 24 | 25 | 26 | 27 | 28 | 29 | 30 | 31 | 32 |
|---|---|---|---|---|---|---|---|---|---|---|---|---|---|---|---|---|
| Rate (kg/ha) | 1.0 | 1.0 | 1.0 | 1.0 | 1.0 | 1.0 | 1.0 | 0.5 | 0.5 | 1.0 | 0.5 | 0.5 | 1.0 | 0.5 | 0.5 | 0.5 |
| Cotton | 70 | 5 | 20 | 5 | 0 | 10 | 90 | 5 | 40 | 40 | 5 | 10 | 90 | 20 | 30 | 100 |
| Soybean | 100 | 40 | 20 | 5 | 95 | 70 | 100 | 95 | 95 | 95 | 95 | 95 | 100 | 100 | 95 | 100 |
| Corn | 100 | 95 | 50 | 20 | 5 | 5 | 100 | 100 | 95 | 90 | 90 | 95 | 100 | 100 | 100 | 95 |
| Rice | 80 | 60 | 10 | 20 | 0 | 5 | 70 | 30 | 80 | 70 | 15 | 90 | 95 | 90 | 90 | 80 |
| Wheat | 90 | 80 | 30 | 0 | 5 | 10 | 80 | 50 | 85 | 85 | 50 | 85 | 95 | 90 | 90 | 90 |
| Morningglory | 100 | 95 | 70 | 10 | 15 | 70 | 100 | 100 | 100 | 100 | 95 | 100 | 100 | 100 | 100 | 100 |
| Wild mustard | 100 | 100 | 100 | 85 | 50 | 100 | 100 | 90 | 100 | 100 | 95 | 100 | 100 | 100 | 100 | 100 |
| Velvetleaf | 100 | 100 | 80 | 90 | 10 | 15 | 100 | 100 | 100 | 100 | 10 | 100 | 100 | 100 | 100 | 100 |
| Barnyardgrass | 95 | 95 | 0 | 30 | 0 | 10 | 100 | 100 | 100 | 70 | 50 | 100 | 100 | 100 | 95 | 95 |
| Green foxtail | 100 | 100 | 30 | 95 | 5 | 5 | 100 | 95 | 100 | 70 | 5 | 90 | 100 | 90 | 95 | 100 |
| Johnsongrass | 100 | 95 | 60 | 60 | 10 | 40 | 100 | 100 | 100 | 100 | 95 | 100 | 100 | 100 | 95 | 95 |

| Compound No. | 33 | 34 | 35 | 36 | 37 | 38 | 39 | 40 | 41 | 42 | 43 | 44 | 45 | 46 | 47 | 48 |
|---|---|---|---|---|---|---|---|---|---|---|---|---|---|---|---|---|
| Rate (kg/ha) | 1.0 | 0.5 | 0.5 | 0.5 | 0.5 | 0.5 | 0.5 | 0.5 | 1.0 | 1.0 | 1.0 | 0.5 | 0.5 | 0.5 | 2.0 | 1.0 |
| Cotton | 15 | 50 | 80 | 5 | 80 | 95 | 50 | 50 | 80 | 89 | 80 | 20 | 70 | 0 | | 80 |
| Soybean | 50 | 100 | 100 | 85 | 100 | 100 | 90 | 85 | 100 | 95 | 80 | 90 | 90 | 5 | 5 | 95 |
| Corn | 90 | 100 | 95 | 80 | 95 | 95 | 95 | 90 | 100 | 100 | 95 | 95 | 95 | 70 | 10 | 90 | 100 |
| Rice | 60 | 70 | 95 | 20 | 70 | 90 | 85 | 60 | 95 | 100 | 70 | 70 | 15 | 0 | | 100 |
| Wheat | 60 | 85 | 90 | 50 | 95 | 90 | 95 | 50 | 100 | 100 | 95 | 50 | 40 | 10 | 40 | 100 |
| Morningglory | 95 | 95 | 100 | 85 | 95 | 100 | 100 | 100 | 100 | 100 | 95 | 95 | 100 | 20 | 80 | 100 |
| Wild mustard | 100 | 100 | 100 | 85 | 100 | 100 | 100 | 100 | 100 | 100 | 100 | 95 | 100 | 95 | | 100 |
| Velvetleaf | 90 | 90 | 100 | 15 | 100 | 100 | 100 | 100 | 100 | 100 | 100 | 100 | 100 | 60 | 90 | 100 |
| Barnyardgrass | 100 | 100 | 95 | 60 | 80 | 100 | 100 | 95 | 100 | 100 | 100 | 95 | 15 | 0 | | 100 |
| Green foxtail | 70 | 95 | 70 | 0 | 85 | 80 | 100 | 85 | 100 | 100 | 200 | 80 | 100 | 40 | 70 | 100 |
| Johnsongrass | 95 | 100 | 95 | 95 | 95 | 100 | 100 | 100 | 100 | 100 | 100 | 100 | 90 | 40 | 85 | 100 |

TABLE 3-continued

PREEMERGENCE HERBICIDAL ACTIVITY (% Control)

| | 49 | 50 | 51 | 52 | 53 | 54 | 55 | 56 | 57 | 58 | 59 | 60 | 61 | 62 | 63 | 64 |
|---|---|---|---|---|---|---|---|---|---|---|---|---|---|---|---|---|
| Blackgrass | | | | | | | | | | | | | | | 70 | |
| Chickweed | | | | | | | | | | | | | | | 0 | |
| Cocklebur | | | | | | | | | | | | | | | 0 | |

| | Compound No. | | | | | | | | | | | | | | | |
|---|---|---|---|---|---|---|---|---|---|---|---|---|---|---|---|---|
| | 49 | 50 | 51 | 52 | 53 | 54 | 55 | 56 | 57 | 58 | 59 | 60 | 61 | 62 | 63 | 64 |
| | Rate (kg/ha) | | | | | | | | | | | | | | | |
| | 0.5 | 0.5 | 0.25 | 0.5 | 1.0 | 1.0 | 0.5 | 0.5 | 1.0 | 1.0 | 0.5 | 0.5 | 0.5 | 1.0 | 0.5 | 0.5 |
| Cotton | 60 | 85 | | 30 | 90 | 90 | 95 | 15 | 90 | 100 | 85 | 10 | 40 | 10 | 50 | 80 |
| Soybean | 80 | 5 | 0 | 0 | 100 | 95 | 100 | 100 | 100 | 100 | 85 | 90 | 85 | 80 | 90 | 90 |
| Corn | 100 | 95 | 15 | 0 | 100 | 90 | 100 | 100 | 100 | 100 | 80 | 60 | 90 | 100 | 95 | 40 |
| Rice | 80 | 85 | | 0 | 95 | 70 | 90 | 40 | 90 | 100 | 70 | 5 | 5 | 50 | 95 | 70 |
| Wheat | 90 | 95 | 0 | 5 | 90 | 90 | 90 | 70 | 100 | 95 | 50 | 10 | 40 | 85 | 95 | 20 |
| Morningglory | 90 | 100 | 80 | 95 | 100 | 100 | 100 | 100 | 100 | 100 | 100 | 100 | 100 | 100 | 100 | 95 |
| Wild mustard | 100 | 100 | | 95 | 100 | 100 | 100 | 100 | 100 | 100 | 100 | 100 | 100 | 100 | 100 | 100 |
| Velvetleaf | 100 | 100 | 15 | 90 | 100 | 100 | 100 | 100 | 100 | 100 | 100 | 100 | 100 | 100 | 100 | 100 |
| Barnyardgrass | 100 | 100 | | 0 | 100 | 90 | 100 | 100 | 100 | 100 | 70 | 50 | 30 | 95 | 95 | 50 |
| Green foxtail | 100 | 100 | 15 | 0 | 100 | 90 | 100 | 100 | 100 | 100 | 85 | 90 | 20 | 60 | 100 | 100 |
| Johnsongrass | 100 | 100 | 15 | 10 | 100 | 100 | 100 | 100 | 100 | 100 | 100 | 10 | 80 | 95 | 95 | 95 |
| Blackgrass | | | 5 | | | | | | | | | | | | | |
| Chickweed | | | 10 | | | | | | | | | | | | | |
| Cocklebur | | | 20 | | | | | | | | | | | | | |

| | Compound No. | | | | | | | | | | | | | | | |
|---|---|---|---|---|---|---|---|---|---|---|---|---|---|---|---|---|
| | 65 | 66 | 67 | 68 | 69 | 70 | 71 | 72 | 73 | 74 | 75 | 76 | 77 | 78 | 79 | 80 |
| | Rate (kg/ha) | | | | | | | | | | | | | | | |
| | 0.5 | 0.5 | 0.5 | 0.5 | 0.5 | 0.5 | 0.5 | 0.5 | 0.5 | 0.5 | 0.5 | 0.5 | 0.5 | 0.5 | 0.5 | 0.5 |
| Cotton | 15 | 5 | 95 | 85 | 95 | 80 | 70 | 65 | | | | 90 | | 50 | 40 | 95 |
| Soybean | 85 | 50 | 95 | 60 | 80 | 70 | 30 | 90 | 80 | 30 | 95 | 90 | 30 | 95 | 90 | 95 |
| Corn | 90 | 50 | 95 | 40 | 40 | 20 | 50 | 90 | 40 | 10 | 40 | 90 | 55 | 60 | 95 | 95 |
| Rice | 20 | 5 | 30 | 70 | 40 | 40 | 15 | 15 | | | | 90 | | 0 | 90 | |
| Wheat | 15 | 10 | 70 | 50 | 10 | 10 | 10 | 50 | 30 | 5 | 45 | 15 | 20 | 20 | 60 | 40 |
| Morningglory | 95 | 100 | 100 | 100 | 100 | 100 | 100 | 100 | 100 | 95 | 100 | 100 | 100 | 100 | 95 | 100 |
| Wild mustard | 100 | 100 | 100 | 100 | 100 | 100 | 100 | 100 | | | | 100 | | 100 | 90 | |
| Velvetleaf | 90 | 100 | 100 | 100 | 100 | 100 | 100 | 100 | 100 | 100 | 100 | 100 | 100 | 100 | 95 | 100 |
| Barnyardgrass | 30 | 70 | 80 | 50 | 50 | 30 | 40 | 85 | | | | 80 | | 50 | 50 | |
| Green foxtail | 85 | 90 | 100 | 95 | 90 | 20 | 95 | 100 | 95 | 15 | 95 | 95 | 85 | 0 | 0 | 75 |
| Johnsongrass | 95 | 95 | 100 | 95 | 90 | 50 | 95 | 100 | 95 | 70 | 90 | 100 | 85 | 100 | 90 | 95 |
| Blackgrass | | | | | | | | | 20 | 20 | 40 | | 65 | | | 70 |
| Chickweed | | | | | | | | | 100 | 100 | 100 | | 95 | | | 30 |
| Cocklebur | | | | | | | | | 95 | 85 | 100 | | 95 | | | |

TABLE 4

POSTEMERGENCE HERBICIDAL ACTIVITY (% Control)

| | Compound No. | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| | Rate (kg/ha) | | | | | | | | | | | | | | | |
| | 0.5 | 0.5 | 0.5 | 1.0 | 0.5 | 1.0 | 0.5 | 0.5 | 0.5 | 0.5 | 0.5 | 1.0 | 1.0 | 1.0 | 1.0 | 1.0 |
| Cotton | 90 | 100 | 80 | 100 | 95 | 100 | 100 | 60 | 95 | 90 | 100 | 50 | 40 | 100 | 100 | 100 |
| Soybean | 90 | 95 | 95 | 80 | 80 | 40 | 90 | 30 | 70 | 40 | 40 | 95 | 70 | 100 | 100 | 100 |
| Corn | 90 | 95 | 95 | 90 | 100 | 85 | 100 | 50 | 70 | 95 | 80 | 95 | 90 | 100 | 100 | 95 |
| Rice | 20 | 30 | 60 | 70 | 5 | 20 | 40 | 5 | 60 | 15 | 40 | 15 | 5 | 70 | 85 | 95 |
| Wheat | 95 | 95 | 70 | 90 | 50 | 60 | 70 | 10 | 40 | 10 | 10 | 15 | 30 | 100 | 95 | 100 |
| Morningglory | 100 | 100 | 100 | 100 | 100 | 95 | 100 | 70 | 100 | 100 | 100 | 100 | 50 | 100 | 100 | 100 |
| Wild mustard | 100 | 100 | 100 | 100 | 100 | 100 | 100 | 10 | 90 | 80 | 95 | 100 | 100 | 100 | 100 | 100 |
| Velvetleaf | 80 | 100 | 100 | 90 | 100 | 100 | 100 | 95 | 100 | 100 | 100 | 100 | 100 | 100 | 100 | 95 |
| Barnyardgrass | 50 | 70 | 60 | 95 | 50 | 50 | 50 | 60 | 70 | 30 | 40 | 60 | 40 | 100 | 100 | 100 |
| Green foxtail | 20 | 50 | 90 | 90 | 5 | 40 | 20 | 40 | 100 | 90 | 10 | 60 | 5 | 100 | 100 | 100 |
| Johnsongrass | 80 | 90 | 85 | 95 | 85 | 95 | 100 | 40 | 95 | 70 | 60 | 60 | 50 | 100 | 100 | 85 |

| | Compound No. | | | | | | | | | | | | | | | |
|---|---|---|---|---|---|---|---|---|---|---|---|---|---|---|---|---|
| | 17 | 18 | 19 | 20 | 21 | 22 | 23 | 24 | 25 | 26 | 27 | 28 | 29 | 30 | 31 | 32 |
| | Rate (kg/ha) | | | | | | | | | | | | | | | |
| | 1.0 | 1.0 | 1.0 | 1.0 | 1.0 | 1.0 | 1.0 | 0.5 | 0.5 | 1.0 | 0.5 | 0.5 | 1.0 | 0.5 | 0.5 | 0.5 |
| Cotton | 100 | 100 | 100 | 70 | 80 | 95 | 100 | 100 | 90 | 60 | 90 | 100 | 95 | 100 | 95 | 100 |
| Soybean | 95 | 60 | 70 | 40 | 85 | 95 | 95 | 95 | 100 | 95 | 95 | 100 | 95 | 100 | 100 | 100 |
| Corn | 95 | 90 | 90 | 40 | 90 | 80 | 100 | 100 | 100 | 100 | 95 | 95 | 100 | 95 | 95 | 100 |
| Rice | 50 | 40 | 30 | 15 | 30 | 20 | 30 | 50 | 70 | 40 | 10 | 70 | 50 | 70 | 70 | 100 |
| Wheat | 85 | 60 | 90 | 20 | 40 | 40 | 95 | 70 | 95 | 85 | 30 | 90 | 95 | 90 | 70 | 100 |
| Morningglory | 100 | 100 | 100 | 60 | 30 | 50 | 100 | 100 | 100 | 100 | 100 | 100 | 100 | 100 | 100 | 100 |
| Wild mustard | 100 | 100 | 100 | 40 | 100 | 95 | 100 | 100 | 100 | 100 | 100 | 100 | 100 | 100 | 100 | 100 |
| Velvetleaf | 100 | 100 | 100 | 95 | 15 | 80 | 100 | 100 | 100 | 100 | 100 | 100 | 100 | 100 | 100 | 100 |
| Barnyardgrass | 100 | 70 | 100 | 70 | 40 | 50 | 100 | 95 | 100 | 95 | 50 | 100 | 100 | 95 | 95 | 100 |
| Green foxtail | 95 | 70 | 95 | 50 | 90 | 70 | 100 | 40 | 95 | 95 | 15 | 100 | 100 | 100 | 85 | 100 |
| Johnsongrass | 100 | 70 | 100 | 50 | 40 | 30 | 100 | 95 | 95 | 100 | 80 | 100 | 100 | 95 | 95 | 100 |

| | Compound No. | | | | | | | | | | | | | | | |
|---|---|---|---|---|---|---|---|---|---|---|---|---|---|---|---|---|
| | 33 | 34 | 35 | 36 | 37 | 38 | 39 | 40 | 41 | 42 | 43 | 44 | 45 | 46 | 47 | 48 |

TABLE 4-continued
POSTEMERGENCE HERBICIDAL ACTIVITY (% Control)

| | \multicolumn{16}{c}{Rate (kg/ha)} |
|---|---|---|---|---|---|---|---|---|---|---|---|---|---|---|---|---|
| | 1.0 | 0.5 | 0.5 | 0.5 | 0.5 | 0.5 | 0.5 | 0.5 | 1.0 | 1.0 | 1.0 | 0.5 | 0.5 | 0.5 | 0.5 | 1.0 |
| Cotton | 100 | 95 | 100 | 80 | 95 | 95 | 100 | 100 | 95 | 95 | 90 | 100 | 90 | 15 | | 8 |
| Soybean | 95 | 95 | 95 | 80 | 100 | 100 | 100 | 95 | 100 | 95 | 90 | 95 | 95 | 50 | 85 | 100 |
| Corn | 90 | 100 | 90 | 100 | 100 | 95 | 95 | 95 | 70 | 90 | 100 | 95 | 40 | 70 | 100 |
| Rice | 30 | 70 | 70 | 15 | 95 | 70 | 80 | 50 | 70 | 40 | 40 | 20 | 20 | 5 | | 70 |
| Wheat | 50 | 90 | 95 | 30 | 95 | 95 | 90 | 70 | 100 | 85 | 70 | 70 | 60 | 10 | 30 | 90 |
| Morningglory | 100 | 100 | 100 | 100 | 100 | 100 | 100 | 100 | 95 | 100 | 100 | 100 | 100 | 50 | 100 | 100 |
| Wild mustard | 100 | 100 | 100 | 100 | 100 | 100 | 100 | 100 | 100 | 90 | 95 | 100 | 95 | 80 | | 100 |
| Velvetleaf | 100 | 100 | 100 | 100 | 100 | 100 | 100 | 100 | 100 | 100 | 100 | 100 | 100 | 100 | 100 | 100 |
| Barnyardgrass | 90 | 100 | 100 | 50 | 100 | 100 | 90 | 100 | 95 | 80 | 50 | 95 | 95 | 20 | | 100 |
| Green foxtail | 95 | 100 | 100 | 50 | 70 | 90 | 70 | 95 | 100 | 90 | 95 | 95 | 95 | 10 | 90 | 100 |
| Johnsongrass | 95 | 100 | 100 | 95 | 100 | 100 | 95 | 100 | 95 | 70 | 95 | 100 | 100 | 20 | 85 | 100 |
| Blackgrass | | | | | | | | | | | | | | 15 | | |
| Chickweed | | | | | | | | | | | | | | 70 | | |
| Cocklebur | | | | | | | | | | | | | | 70 | | |

| | \multicolumn{16}{c}{Compound No.} |
|---|---|---|---|---|---|---|---|---|---|---|---|---|---|---|---|---|
| | 49 | 50 | 51 | 52 | 53 | 54 | 55 | 56 | 57 | 58 | 59 | 60 | 61 | 62 | 63 | 64 |
| | \multicolumn{16}{c}{Rate (kg/ha)} |
| | 0.5 | 0.5 | 0.25 | 0.5 | 1.0 | 0.5 | 0.5 | 0.5 | 1.0 | 1.0 | 0.5 | 0.5 | 0.5 | 1.0 | 0.5 | 0.5 |
| Cotton | 95 | 95 | | 95 | 100 | 95 | 100 | 100 | 100 | 100 | 100 | 100 | 100 | 100 | 100 | 90 |
| Soybean | 100 | 95 | 90 | 90 | 95 | 95 | 100 | 100 | 100 | 100 | 90 | 100 | 95 | 100 | 95 | 95 |
| Corn | 100 | 85 | 60 | 70 | 95 | 100 | 100 | 100 | 100 | 100 | 100 | 100 | 100 | 95 | 95 | 95 |
| Rice | 50 | 60 | | 5 | 85 | 30 | 95 | 95 | 100 | 100 | 90 | 50 | 10 | 15 | 90 | 50 |
| Wheat | 85 | 80 | 20 | 30 | 85 | 95 | 100 | 100 | 100 | 100 | 95 | 100 | 40 | 90 | 95 | 90 |
| Morningglory | 100 | 100 | 100 | 100 | 100 | 100 | 100 | 100 | 100 | 100 | 100 | 100 | 100 | 100 | 100 | 100 |
| Wild mustard | 100 | 100 | | 100 | 100 | 100 | 100 | 100 | 100 | 100 | 100 | 90 | 100 | 100 | 95 | 100 |
| Velvetleaf | 100 | 100 | 95 | 100 | 100 | 100 | 100 | 100 | 100 | 100 | 100 | 100 | 100 | 100 | 100 | 100 |
| Barnyardgrass | 100 | 100 | | 20 | 100 | 80 | 100 | 100 | 100 | 100 | 100 | 95 | 95 | 95 | 90 | 95 |
| Green foxtail | 100 | 95 | 40 | 30 | 100 | 100 | 100 | 100 | 100 | 100 | 90 | 50 | 90 | 100 | 70 | 70 |
| Johnsongrass | 95 | 100 | | 30 | 100 | 100 | 100 | 100 | 100 | 100 | 100 | 90 | 90 | 100 | 90 | 100 |
| Blackgrass | | | 40 | | | | | | | | | | | | | |
| Chickweed | | | 90 | | | | | | | | | | | | | |
| Cocklebur | | | 90 | | | | | | | | | | | | | |

| | \multicolumn{16}{c}{Compound No.} |
|---|---|---|---|---|---|---|---|---|---|---|---|---|---|---|---|---|
| | 65 | 66 | 67 | 68 | 69 | 70 | 71 | 72 | 73 | 74 | 75 | 76 | 77 | 78 | 79 | 80 |
| | \multicolumn{16}{c}{Rate (kg/ha)} |
| | 0.5 | 0.5 | 0.5 | 0.5 | 0.5 | 0.5 | 0.5 | 0.5 | 0.5 | 0.5 | 0.5 | 0.5 | 0.125 | 0.25 | 0.5 | 0.5 |
| Cotton | 70 | 100 | 100 | 100 | 100 | 95 | 100 | 100 | | | | 100 | | 100 | 100 | |
| Soybean | 95 | 90 | 100 | 95 | 85 | 90 | 95 | 70 | 80 | 95 | 60 | 95 | 90 | 85 | 95 | 60 |
| Corn | 95 | 100 | 100 | 100 | 100 | 100 | 100 | 100 | 5 | 100 | 30 | 100 | 30 | 90 | 95 | 40 |
| Rice | 50 | 5 | 90 | 50 | 30 | 5 | 70 | 5 | | | | 40 | | 20 | 70 | |
| Wheat | 70 | 60 | 100 | 95 | 95 | 90 | 95 | 100 | 30 | — | 60 | 95 | 15 | 90 | 90 | 30 |
| Morningglory | 100 | 100 | 100 | 100 | 100 | 100 | 100 | 100 | 80 | 100 | 100 | 100 | 100 | 100 | 100 | 100 |
| Wild mustard | 100 | 100 | 100 | 100 | 100 | 100 | 100 | 100 | | | | 100 | | 100 | 100 | |
| Velvetleaf | 100 | 100 | 100 | 100 | 100 | 100 | 95 | 100 | 90 | 100 | 100 | 100 | 100 | 90 | 100 | 100 |
| Barnyardgrass | 50 | 70 | 100 | 90 | 50 | 85 | 30 | 85 | | | | 95 | | 100 | 80 | |
| Green foxtail | 20 | 80 | 100 | 100 | 100 | 100 | 50 | 95 | | 100 | 100 | 100 | 70 | 80 | 95 | 80 |
| Johnsongrass | 95 | 70 | 100 | 95 | 90 | 60 | 80 | 85 | | 95 | 95 | 80 | 10 | 70 | 90 | 70 |
| Blackgrass | | | | | | | | | 10 | 85 | 10 | | 15 | | | 30 |
| Chickweed | | | | | | | | | 100 | 100 | 100 | | 70 | | | 0 |
| Cocklebur | | | | | | | | | 95 | 100 | 100 | | 95 | | | 95 |

I claim:

1. A herbicidal compound of the formula

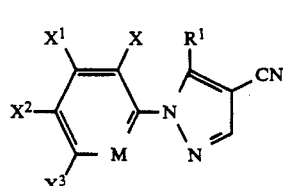

wherein X is chlorine or fluorine, $X^1$ is hydrogen, chlorine, or fluorine, $X^2$ is chlorine, fluorine, trifluoromethyl, or ethoxy, and $X^3$ is hydrogen, chlorine, or fluorine, or $CH_2$—$N(CH_3(CH_2C\equiv CH)$; M is —N—; and $R^1$ is —CH=C(—$R^2$)—C(=O)—Z—[S(O)$_2$]$_n$—$R^3$ wherein $R^2$ is hydrogen or methyl; Z is —O—, —S— or —$NR^4$; and n is 0 or 1;

when Z is —O— or —S— and n is 0, $R^3$ is hydrogen, sodium, lower alkyl, cyanomethyl, propargyl, yl, phenylmethyl optionally substituted in the 4-position with methylthio, and —$R^5$—$COR^6$, where $R^5$ is a divalent alkylene of 1 to 3 carbons and $R^6$ is hydrogen, amino, dimethylamino, methylsulfonylamino, or an alkoxy of 1 to 4 carbons; p1 when Z is $NR^4$— and n is 0, $R^3$ is hydrogen, lower alkyl, methoxy, 1-cyanoethyl, 1-(ethoxycarbonyl)methyl, phenylmethyl, and phenyl; and $R^4$ is hydrogen, methyl, or —$C_2H_5OC_2H_5$— taken with $R^3$ to form a morpholine ring;

when Z is —$NR^4$— and n is 1, $R^3$ is lower alkyl, trifluoromethyl, cyclohexylmethyl, 2-phenylethyl, 2-phenylethenyl, amino, d-10-camphoryl, 3,5-dimethylisoxazol-4-yl, phenylmethyl optionally substituted with one or more of chlorine, bromine, fluorine, or methyl, and phenyl optionally substituted with chlorine or methyl; and $R^4$ is hydrogen;

in addition, when $R^2$ is hydrogen and $R^3$ is lower alkyl or phenylmethyl, $R^4$ may be sodium.

2. A compound of claim 1 in which X is chlorine, $X^1$ is hydrogen or chlorine, $X^2$ is chlorine or trifluoromethyl, and $X^3$ is hydrogen; and Z is —O— or —$NR^4$.

3. A compound of claim 2 in which Z is —O—, n is 0, and $R^3$ is hydrogen, sodium, ethyl, phenyl or —$R^5$—$COR^6$ in which $R^6$ is hydroxy or an alkoxy of 1 to 4 carbons.

4. A compound of claim 2 in which Z is —$NR^4$—, n is 0; $R^3$ is hydrogen, lower alkyl, ethoxycarbonylmethyl, phenylmethyl, or phenyl; and $R^4$ is hydrogen, methyl, or taken with $R^3$ —$C_2H_5OC_2H_5$— to form a morpholine ring.

5. A compound of claim 2 in which Z is —$NR^4$—, n is 1, and $R^3$ is lower alkyl of 1 to 4 carbon atoms, or phenylmethyl optionally substituted with one or two of chlorine or methyl; and $R^4$ is hydrogen; in addition when $R^2$ is hydrogen, and $R^3$ is methyl, 1-methylethyl, or phenylmethyl, $R^4$ may also be sodium.

6. A compound of claim 2 in which M is —N—, X is chlorine, $X^1$, $X^3$, $R^2$, and $R^4$ are hydrogen, and $X^2$ is trifluoromethyl.

7. A compound of claim 6 in which Z is —O—, n is 0, $R^3$ is hydrogen, sodium, methyl, ethyl, carboxymethyl, 1-carboxyethyl, methoxycarbonylmethyl, ethoxycarbonylmethyl, 1,1-dimethylethoxycarbonylmethyl, 1-(methoxycarbonyl)ethyl, 1-(1,1-dimethylethoxycarbonyl)ethyl, or phenylmethyl.

8. A compound of claim 6 in which Z is —$NR^4$—, n is 0, $R^3$ is hydrogen, methyl, or 1-methylpropyl; and $R^4$ is hydrogen or methyl.

9. A compound of claim 6, in which Z is —$NR^4$—, and n is 1, $R^3$ is lower alkyl of 1 to 4 carbon atoms or phenylmethyl; and $R^4$ is hydrogen; in addition when $R^2$ is hydrogen, and $R^3$ is methyl, $R^4$ may also be sodium.

10. The compound of claim 9 in which $R^3$ is phenylmethyl.

11. An herbicidal composition comprising an herbicidally effective amount of a compound of claim 1 in admixture with a suitable carrier.

12. A method for controlling undesired plant growth which comprises applying to the locus where control is desired an herbicidally effective amount of a composition of claim 11.

* * * * *